US008936586B2

(12) United States Patent
Roe

(10) Patent No.: US 8,936,586 B2
(45) Date of Patent: Jan. 20, 2015

(54) ERGONOMIC GRASPING AIDS FOR REUSABLE PULL-ON OUTER COVERS

(71) Applicant: The Procter & Gamble Company, Cincinnati, OH (US)

(72) Inventor: Donald Carroll Roe, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 146 days.

(21) Appl. No.: 13/789,711

(22) Filed: Mar. 8, 2013

(65) Prior Publication Data
US 2014/0257227 A1    Sep. 11, 2014

(51) Int. Cl.
A61F 13/15    (2006.01)

(52) U.S. Cl.
USPC ............ 604/385.14; 604/385.15; 604/385.24; 604/385.29; 604/385.16

(58) Field of Classification Search
USPC ............. 604/385.14, 385.15, 385.24, 385.29, 604/385.16
See application file for complete search history.

(56) References Cited

U.S. PATENT DOCUMENTS

| 2,119,610 | A | 6/1938 | Robert |
|---|---|---|---|
| 2,530,647 | A | 11/1950 | Buehler |
| 2,688,328 | A | 9/1954 | Marcus |
| 2,793,642 | A | 5/1957 | Andruhovici |
| 3,077,193 | A | 2/1963 | Mann |
| 3,496,259 | A | 2/1970 | Guenther |
| 3,560,292 | A | 2/1971 | Butter |
| 3,719,736 | A | 3/1973 | Woodruff |
| 3,735,424 | A | 5/1973 | Maggio et al. |
| 3,860,003 | A | 1/1975 | Buell |
| 3,911,173 | A | 10/1975 | Sprague, Jr. |
| 3,926,189 | A | 12/1975 | Taylor |
| 3,929,135 | A | 12/1975 | Thompson |
| 3,955,575 | A | 5/1976 | Okuda |
| 4,022,210 | A | 5/1977 | Glassman |
| 4,072,150 | A | 2/1978 | Glassman |
| 4,081,301 | A | 3/1978 | Buell |
| 4,116,892 | A | 9/1978 | Schwarz |

(Continued)

FOREIGN PATENT DOCUMENTS

| AU | 642 386 | 10/1993 |
|---|---|---|
| CA | 2 103 537 | 2/1995 |

(Continued)

OTHER PUBLICATIONS www.gdiapers.com—Web pages dated Nov. 23, 2009.

(Continued)

Primary Examiner — Jacqueline F. Stephens
(74) Attorney, Agent, or Firm — Christian M. Best

(57) ABSTRACT

A reusable outer cover is provided. The reusable outer cover is configured for use with a disposable absorbent insert to together form a wearable absorbent article. The reusable outer cover may be configured as a pull-on pant and may include a front waist region, a rear waist region, a crotch region disposed intermediate the front waist region and the rear waist region, and a wearer-facing surface. The wearer-facing surface of the front waist region or the rear waist region may include an insert fastener component. The reusable outer cover may further include a grasping aid configured to assist in the application of the article onto a wearer. The grasping aid may be force-coupled to the insert fastener component or to a reduced elongation zone in the reusable outer cover.

21 Claims, 20 Drawing Sheets

(56) References Cited

U.S. PATENT DOCUMENTS

| | | |
|---|---|---|
| 4,195,634 A | 4/1980 | DiSalvo et al. |
| 4,223,059 A | 9/1980 | Schwarz |
| 4,265,245 A | 5/1981 | Glassman |
| 4,284,454 A | 8/1981 | Joa |
| 4,324,246 A | 4/1982 | Mullane et al. |
| 4,326,302 A | 4/1982 | Lowe et al. |
| 4,338,939 A | 7/1982 | Daville |
| 4,342,314 A | 8/1982 | Radel et al. |
| 4,352,356 A | 10/1982 | Tong |
| 4,438,167 A | 3/1984 | Schwarz |
| 4,463,045 A | 7/1984 | Ahr et al. |
| 4,475,912 A | 10/1984 | Coates |
| 4,496,360 A | 1/1985 | Joffe et al. |
| 4,573,986 A | 3/1986 | Minetola et al. |
| 4,578,073 A | 3/1986 | Dysart et al. |
| 4,579,556 A | 4/1986 | Mcfarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,615,695 A | 10/1986 | Cooper |
| 4,625,245 A | 11/1986 | White |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,704,116 A | 11/1987 | Enloe |
| 4,710,187 A | 12/1987 | Boland et al. |
| 4,747,846 A | 5/1988 | Boland et al. |
| 4,756,709 A | 7/1988 | Stevens |
| 4,770,656 A | 9/1988 | Proxmire et al. |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,955,880 A | 9/1990 | Rodriquez |
| 4,961,736 A | 10/1990 | McCloud |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | Desmarais et al. |
| 5,261,901 A | 11/1993 | Guay |
| 5,269,775 A | 12/1993 | Freeland et al. |
| 5,283,910 A | 2/1994 | Flint |
| 5,296,184 A | 3/1994 | Wu et al. |
| 5,306,267 A | 4/1994 | Hahn et al. |
| 5,342,338 A | 8/1994 | Roe |
| 5,354,597 A | 10/1994 | Capik et al. |
| 5,360,422 A | 11/1994 | Brownlee et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,458,591 A | 10/1995 | Roessler et al. |
| 5,476,457 A | 12/1995 | Roessler et al. |
| 5,509,915 A | 4/1996 | Hanson et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A | 10/1996 | Peterson |
| 5,571,096 A | 11/1996 | Dobrin et al. |
| 5,607,760 A | 3/1997 | Roe |
| 5,609,587 A | 3/1997 | Roe |
| 5,613,959 A | 3/1997 | Roessler et al. |
| 5,624,425 A | 4/1997 | Gray et al. |
| 5,624,429 A * | 4/1997 | Long et al. .................... 604/391 |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kj.ae butted.rgaard et al. |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,795,348 A | 8/1998 | Roe et al. |
| 5,814,037 A | 9/1998 | Coates |
| 5,827,261 A | 10/1998 | Osborn et al. |
| 5,843,065 A | 12/1998 | Wyant |
| 5,843,267 A | 12/1998 | Cashaw et al. |
| 5,846,232 A | 12/1998 | Serbiak et al. |
| H1788 H | 2/1999 | Christon et al. |
| 5,865,823 A | 2/1999 | Curro |
| 5,906,603 A | 5/1999 | Roe et al. |
| 5,911,713 A | 6/1999 | Yamada et al. |
| 5,938,648 A | 8/1999 | Lavon et al. |
| 5,941,864 A | 8/1999 | Roe |
| 5,947,946 A | 9/1999 | Fisher et al. |
| 5,968,025 A | 10/1999 | Roe et al. |
| 5,984,911 A | 11/1999 | Siebers et al. |
| 6,007,528 A | 12/1999 | Osborn |
| 6,010,491 A | 1/2000 | Roe et al. |
| 6,120,487 A | 9/2000 | Ashton |
| 6,142,983 A | 11/2000 | Suprise et al. |
| 6,207,738 B1 | 3/2001 | Zuckerman et al. |
| 6,213,991 B1 * | 4/2001 | Kling et al. ............. 604/385.01 |
| 6,229,061 B1 | 5/2001 | Dragoo et al. |
| 6,240,569 B1 | 6/2001 | Van Gompel et al. |
| 6,251,097 B1 | 6/2001 | Kline et al. |
| 6,254,583 B1 | 7/2001 | Coates |
| 6,258,308 B1 | 7/2001 | Brady et al. |
| 6,278,037 B1 | 8/2001 | Schmidt et al. |

(56) References Cited

U.S. PATENT DOCUMENTS

| | | |
|---|---|---|
| 6,287,169 B1 | 9/2001 | Willms et al. |
| 6,291,039 B1 | 9/2001 | Combe et al. |
| 6,307,119 B1 | 10/2001 | Cammarota et al. |
| 6,368,444 B1 | 4/2002 | Jameson et al. |
| 6,414,215 B1 | 7/2002 | Roe |
| 6,420,627 B1 | 7/2002 | Ohnishi et al. |
| 6,423,042 B1 | 7/2002 | Sasaki |
| 6,423,043 B1 | 7/2002 | Gustafsson |
| 6,432,098 B1 | 8/2002 | Kline et al. |
| 6,468,257 B1 | 10/2002 | Ono et al. |
| 6,482,191 B1 | 11/2002 | Roe et al. |
| 6,514,362 B1 | 2/2003 | Zuckerman et al. |
| 6,526,631 B1 | 3/2003 | Alberg et al. |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,575,951 B1 | 6/2003 | Ono et al. |
| 6,579,273 B2 | 6/2003 | Dupuy |
| 6,623,466 B1 | 9/2003 | Richardson |
| 6,669,618 B2 | 12/2003 | Reising et al. |
| 6,680,422 B2 | 1/2004 | Roe |
| 6,709,423 B1 | 3/2004 | Herrlein et al. |
| 6,716,441 B1 | 4/2004 | Osborne et al. |
| 6,764,477 B1 | 7/2004 | Chen et al. |
| 6,764,478 B2 | 7/2004 | Ashton et al. |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,921,393 B2 | 7/2005 | Tears et al. |
| 6,936,039 B2 | 8/2005 | Kline et al. |
| 6,964,720 B2 | 11/2005 | Schneider et al. |
| 6,966,720 B2 | 11/2005 | Moss |
| 6,980,872 B2 | 12/2005 | Kano et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,166,095 B1 | 1/2007 | Coates |
| 7,211,531 B2 | 5/2007 | Schneider et al. |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,344,526 B2 | 3/2008 | Yang et al. |
| 7,387,620 B2 | 6/2008 | Watanabe et al. |
| 7,407,468 B2 | 8/2008 | Reising et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Franke et al. |
| 7,537,587 B2 | 5/2009 | Carstens |
| 7,576,019 B2 | 8/2009 | Bond et al. |
| 7,591,811 B2 | 9/2009 | Wilkinson |
| 7,629,501 B2 | 12/2009 | Labit et al. |
| 7,666,175 B2 | 2/2010 | Trennepohl |
| 7,695,463 B2 | 4/2010 | Lavon et al. |
| 7,771,406 B2 | 8/2010 | Mueller et al. |
| 7,771,408 B2 | 8/2010 | Mueller et al. |
| 7,776,770 B2 | 8/2010 | Wang et al. |
| 7,776,771 B2 | 8/2010 | Autran et al. |
| 7,820,875 B2 | 10/2010 | Roe et al. |
| 7,824,387 B2 | 11/2010 | LaVon |
| 7,833,211 B2 | 11/2010 | Mansfield |
| 7,842,627 B2 | 11/2010 | Gao et al. |
| 7,872,169 B2 | 1/2011 | Ruiz et al. |
| 7,875,014 B2 | 1/2011 | Hendren et al. |
| 7,887,527 B2 | 2/2011 | Hayashi et al. |
| 7,914,507 B1 | 3/2011 | Magee |
| 7,985,210 B2 | 7/2011 | Ashton et al. |
| 7,993,322 B2 | 8/2011 | Brud et al. |
| 8,062,276 B2 | 11/2011 | Labit et al. |
| 8,066,685 B2 | 11/2011 | Olson et al. |
| 8,118,801 B2 | 2/2012 | Macura et al. |
| 8,158,043 B2 | 4/2012 | Gibson et al. |
| 8,206,366 B2 | 6/2012 | Datta et al. |
| 8,262,635 B2 | 9/2012 | Labit et al. |
| 8,377,023 B2 | 2/2013 | Sawyer et al. |
| 8,568,380 B2 | 10/2013 | Brownlee |
| 8,585,667 B2 | 11/2013 | Roe et al. |
| 2002/0010452 A1 | 1/2002 | Dupuy |
| 2002/0035747 A1 | 3/2002 | Kusibojoska et al. |
| 2002/0045874 A1 | 4/2002 | Kumasaka et al. |
| 2002/0076520 A1 | 6/2002 | Neeb et al. |
| 2002/0128619 A1 | 9/2002 | Carlbark et al. |
| 2003/0055394 A1* | 3/2003 | Gibbs .......................... 604/389 |
| 2003/0088220 A1 | 5/2003 | Molander et al. |
| 2003/0091807 A1 | 5/2003 | Desai et al. |
| 2003/0114805 A1 | 6/2003 | Rainville-Lonn et al. |
| 2003/0125701 A1 | 7/2003 | Widlund |
| 2003/0163104 A1 | 8/2003 | Tears et al. |
| 2003/0233082 A1 | 12/2003 | Kline et al. |
| 2004/0023771 A1 | 2/2004 | Reising et al. |
| 2004/0030311 A1 | 2/2004 | Suzuki et al. |
| 2004/0127867 A1 | 7/2004 | Odorzynski et al. |
| 2005/0033258 A1 | 2/2005 | Suzuki et al. |
| 2005/0096624 A1 | 5/2005 | Hoshino et al. |
| 2005/0148974 A1 | 7/2005 | Datta et al. |
| 2005/0164587 A1 | 7/2005 | Melik et al. |
| 2005/0175269 A1 | 8/2005 | Ashton et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2006/0035055 A1 | 2/2006 | Schneider et al. |
| 2006/0047260 A1 | 3/2006 | Ashton et al. |
| 2006/0058766 A1 | 3/2006 | Mueller et al. |
| 2006/0069372 A1 | 3/2006 | Chakravarty et al. |
| 2006/0087053 A1 | 4/2006 | O'Donnell et al. |
| 2006/0095012 A1 | 5/2006 | Cohen |
| 2006/0107505 A1 | 5/2006 | Desai et al. |
| 2006/0129114 A1 | 6/2006 | Mason et al. |
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1 | 10/2006 | Lavon |
| 2006/0247599 A1 | 11/2006 | Mullen et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 | 11/2006 | Carstens |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0123834 A1 | 5/2007 | McDowall et al. |
| 2007/0142798 A1 | 6/2007 | Goodlander et al. |
| 2007/0142816 A1 | 6/2007 | Carstens |
| 2007/0191806 A1 | 8/2007 | Mueller et al. |
| 2007/0203301 A1 | 8/2007 | Autran et al. |
| 2007/0239130 A1 | 10/2007 | Trennepohl |
| 2007/0249254 A1 | 10/2007 | Mansfield |

(56) References Cited

U.S. PATENT DOCUMENTS

| | | |
|---|---|---|
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdonl et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Mueller et al. |
| 2008/0045917 A1 | 2/2008 | Autran et al. |
| 2008/0081854 A1 | 4/2008 | Wang et al. |
| 2008/0108963 A1 | 5/2008 | Ashton et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0119816 A1 | 5/2008 | Carstens |
| 2008/0125739 A1 | 5/2008 | Lodge et al. |
| 2008/0188822 A1 | 8/2008 | Lodge et al. |
| 2008/0215027 A1 | 9/2008 | Labit et al. |
| 2008/0215028 A1 | 9/2008 | Brown et al. |
| 2008/0224351 A1 | 9/2008 | Curro et al. |
| 2008/0287983 A1 | 11/2008 | Smith et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0069722 A1 | 3/2009 | Flaction et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0127742 A1 | 5/2009 | Qureshi et al. |
| 2009/0216209 A1 | 8/2009 | Ekstrom |
| 2010/0004616 A1 | 1/2010 | Nakamura et al. |
| 2010/0005570 A1 | 1/2010 | Rachman |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2010/0331803 A1 | 12/2010 | Saito |
| 2011/0137277 A1 | 6/2011 | Hough et al. |
| 2011/0172622 A1 | 7/2011 | Roe et al. |
| 2011/0288518 A1 | 11/2011 | Roe et al. |
| 2012/0022485 A1 | 1/2012 | Roe et al. |
| 2012/0022491 A1 | 1/2012 | Roe |
| 2012/0049404 A1 | 3/2012 | Gibson et al. |
| 2013/0226122 A1 | 8/2013 | Roe et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |

FOREIGN PATENT DOCUMENTS

| | | |
|---|---|---|
| CA | 2221209 | 11/1996 |
| CA | 2 365 577 | 6/2003 |
| DE | 103 03 903 | 11/2003 |
| EP | 0 023 804 | 2/1981 |
| EP | 0 187 726 | 7/1986 |
| EP | 319314 | 6/1989 |
| EP | 0667136 | 8/1995 |
| EP | 549988 | 6/1998 |
| EP | 796069 | 8/2000 |
| EP | 763353 | 6/2002 |
| FR | 2532337 | 3/1984 |
| GB | 112638 | 1/1918 |
| GB | 2 440 314 | 1/2008 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 62-110903 | 7/1987 |
| JP | 03-091325 | 1/1990 |
| JP | 4-7792 | 11/1990 |
| JP | 06-178795 | 1/1993 |
| JP | H11104180 | 4/1999 |
| JP | 2001-346826 | 12/2001 |
| JP | 2002-325786 | 11/2002 |
| JP | 2003-038564 | 2/2003 |
| JP | 2003-093438 | 4/2003 |
| JP | 2003-190213 | 7/2003 |
| JP | 2004-261332 | 9/2004 |
| JP | 2005-6827 | 1/2005 |
| JP | 2005-111119 | 4/2005 |
| JP | 2005-118533 | 5/2005 |
| JP | 3109189 | 5/2005 |
| JP | 2007-244506 | 3/2006 |
| JP | 2008-237231 | 10/2008 |
| JP | 2009-153736 | 7/2009 |
| JP | 47-40720 | 8/2011 |
| WO | WO-90/08524 | 8/1990 |
| WO | WO-91/16871 | 11/1991 |
| WO | WO-92/01431 | 2/1992 |
| WO | WO-92/15444 | 9/1992 |
| WO | WO-94/15563 | 7/1994 |
| WO | WO-94/15663 | 7/1994 |
| WO | WO-95/10992 | 4/1995 |
| WO | WO-95/16746 | 6/1995 |
| WO | WO-96/17572 | 6/1996 |
| WO | WO-96/24319 | 8/1996 |
| WO | WO-96/32912 | 10/1996 |
| WO | WO-00/65348 | 11/2000 |
| WO | WO-02/066086 | 8/2002 |
| WO | WO-2004/060229 | 7/2004 |
| WO | WO-2005/039469 | 5/2005 |
| WO | WO-2005/052052 | 6/2005 |
| WO | WO-2005/096855 | 10/2005 |
| WO | WO-2005/097031 | 10/2005 |
| WO | WO-2008/030984 | 3/2008 |
| WO | WO-2008/120959 | 10/2008 |
| WO | WO-2008/142634 | 11/2008 |
| WO | WO-2010/053006 | 5/2010 |
| WO | WO-2010/078661 | 7/2010 |
| WO | WO-2012/167844 | 12/2012 |
| WO | WO-2013/059533 | 4/2013 |

OTHER PUBLICATIONS www.fuzzibunz.com—Web pages dated Nov. 23, 2009.

(56) References Cited

OTHER PUBLICATIONS www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
All Office Actions, U.S. Appl. No. 13/789,707.
All Office Actions, U.S. Appl. No. 13/789,709.
All Office Actions, U.S. Appl. No. 13/789,731.
All Office Actions, U.S. Appl. No. 13/789,735.
All Office Actions, U.S. Appl. No. 13/789,738.
37 photographs (obtained from Marketing Technology Service, Inc.) of a product believed to be a product of Kao Corp. and sold in Japan in 1986.
International Search Report and Written Opinion, PCT/US2014/020808, date of mailing May 16, 2014.

\* cited by examiner

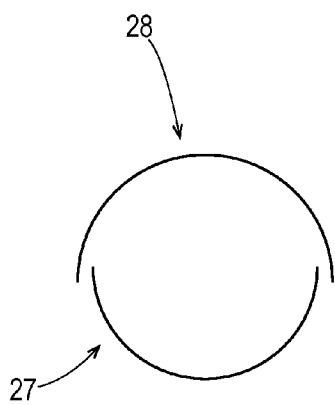 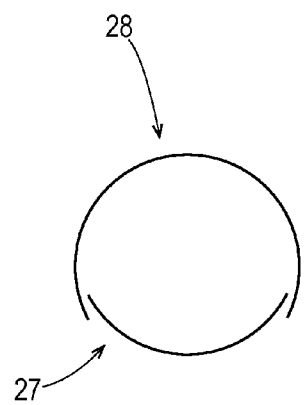 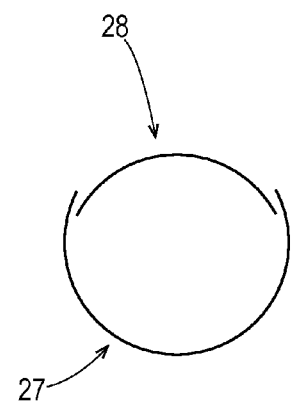
Fig. 1E        Fig. 1F        Fig. 1G
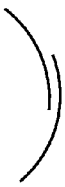 
Fig. 1H        Fig. 1I

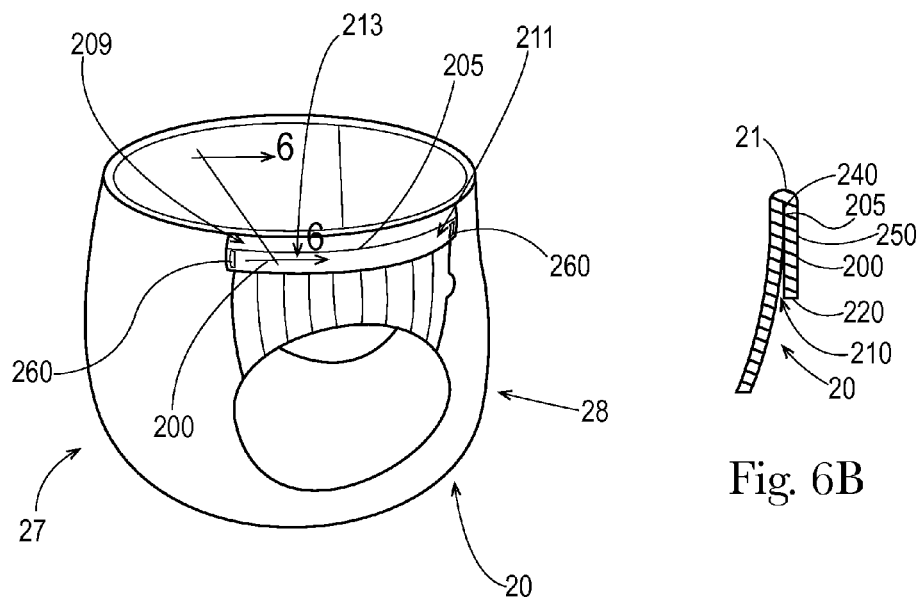
Fig. 6A
Fig. 6B
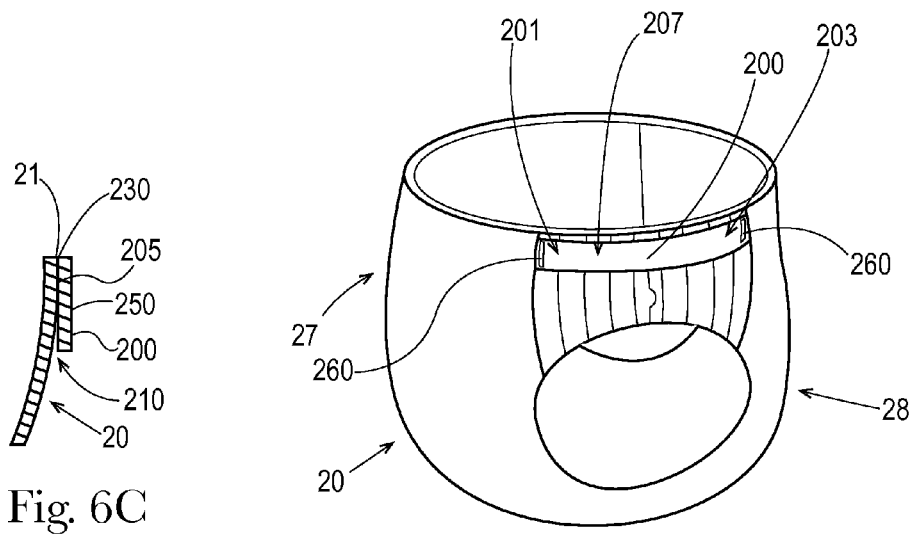
Fig. 6C
Fig. 6D

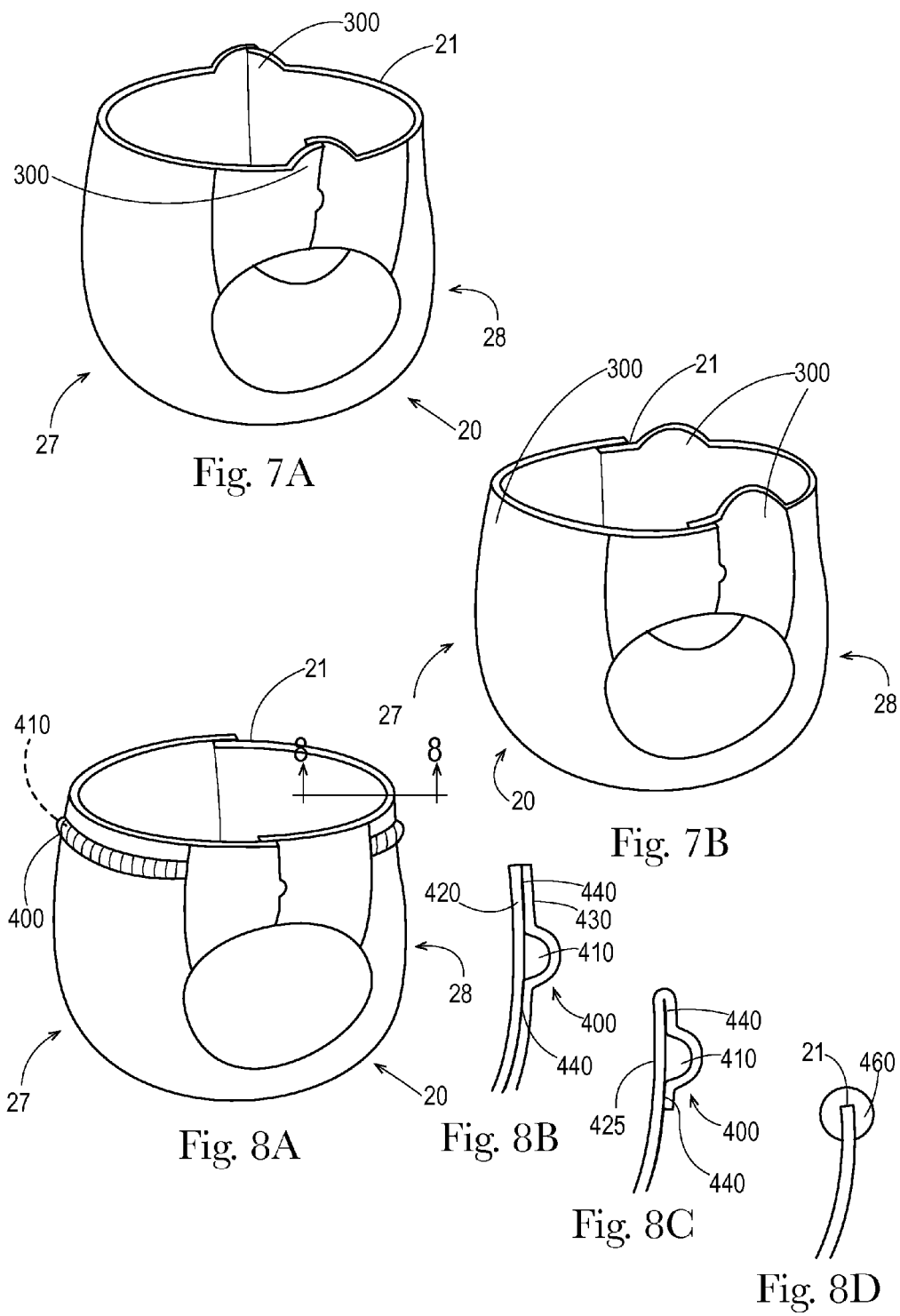

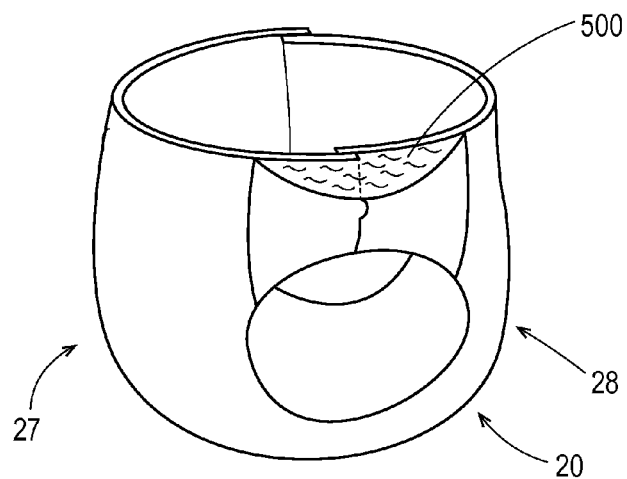
Fig. 9A
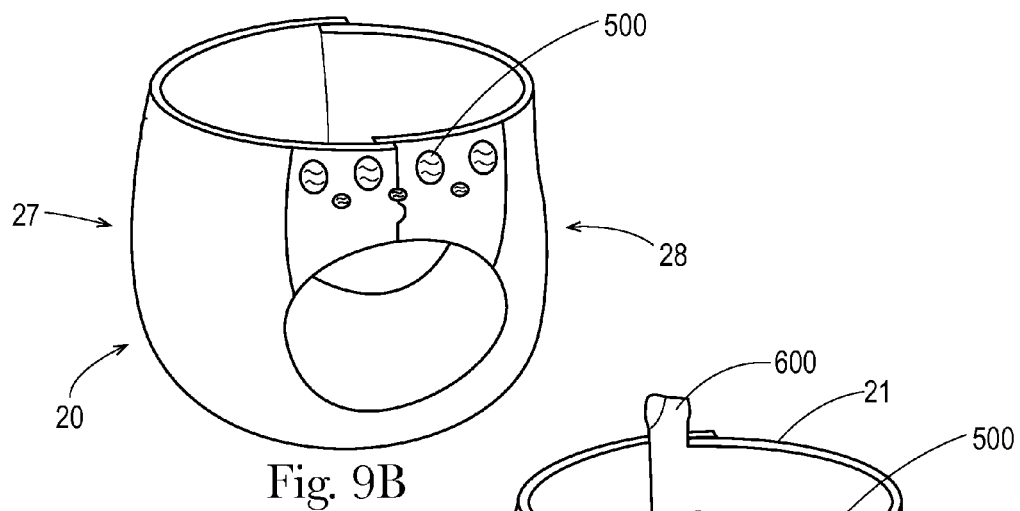
Fig. 9B
Fig. 10
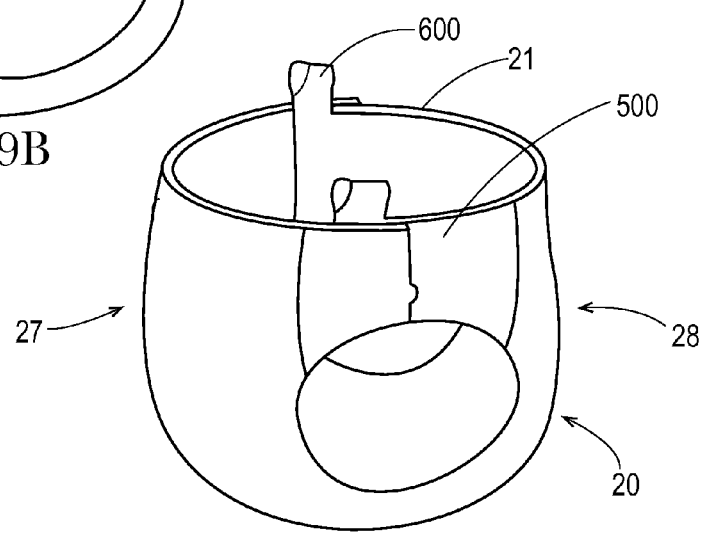

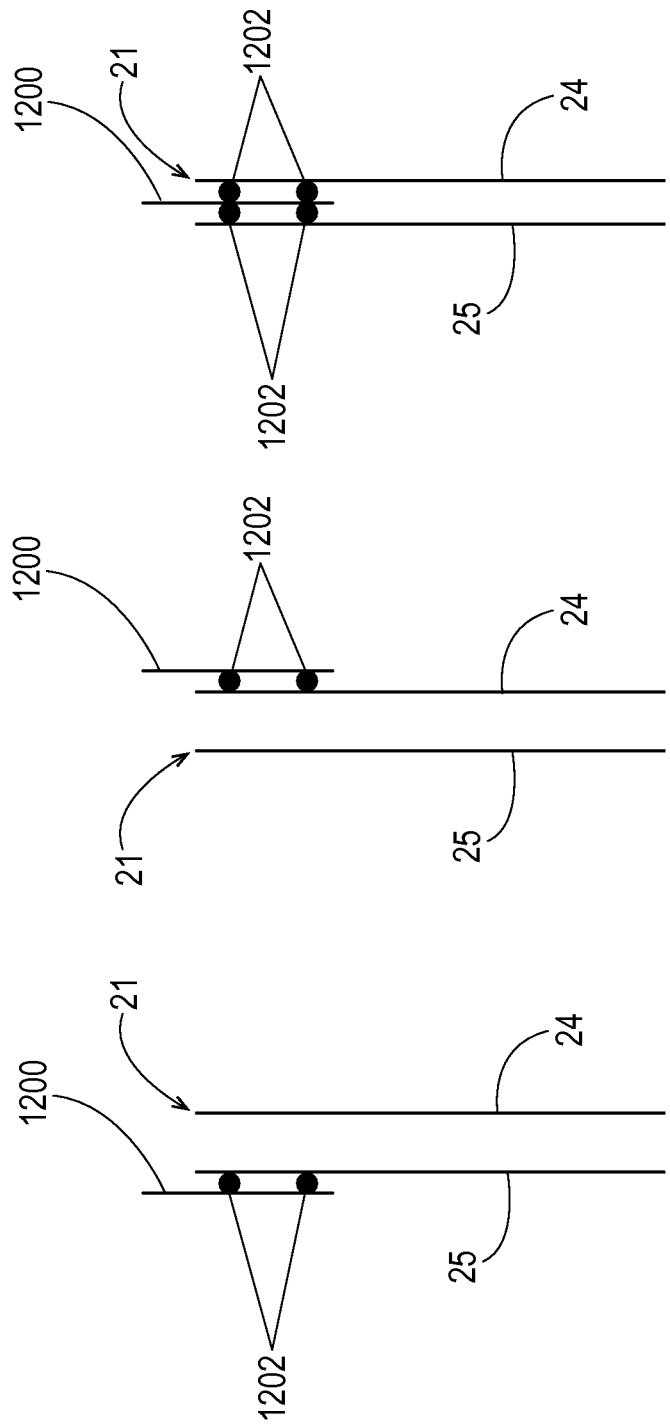

ERGONOMIC GRASPING AIDS FOR REUSABLE PULL-ON OUTER COVERS

FIELD

The present disclosure generally relates to the field of wearable absorbent articles having features for the containment and absorption of bodily exudates, and more particularly, to such wearable absorbent articles having disposable absorbent inserts configured to be attached to pull-on reusable outer covers, wherein the pull-on reusable outer covers comprise certain ergonomic grasping aids.

BACKGROUND

In general, disposable absorbent inserts may be engaged with reusable outer covers to form wearable absorbent articles, such as a pull-on pant diaper or a pull-on adult incontinence pant. Such wearable absorbent articles offer the benefit of receiving and containing urine and other bodily exudates. To effectively contain these bodily exudates, the articles should provide a snug fit around the waist and legs of the wearer. Conventional taped diapers generally contain front and rear waist regions that are releasably connected by fasteners. Application of conventional taped diapers is usually performed by a caregiver when the wearer is in a supine position. Such taped diapers allow for easy application by the caregiver, but may prohibit self-application by the wearer or difficult application by a caregiver when the wearer is in a standing position.

Disposable pull-on pants were developed, in part, to address the problem of self-application or removal by the wearer and/or application to standing wearers. Disposable pull-on pants effectively contain exudates while allowing self-application or removal or application/removal for standing changes. Such disposable pull-on pants generally include a waist opening, two leg openings, and a pair of side seams that are prejoined thus connecting the front and rear waist regions of the pant. The chassis of these pants typically comprises a liquid pervious topsheet, a liquid impervious backsheet, and an absorbent core positioned therebetween. An additional benefit of pull-on pants is that they serve as an intermediary between conventional taped diaper use and full toilet training. The pull-on pant is intended for use when a child has reached an age where he or she is ready to graduate to an underpant-type garment as a replacement for disposable taped diapers. The pull-on pant provides a milestone for the child who is developing independence from the caregiver. Such benefits can also be realized by adult incontinence individuals. A suitable pull-on pant, however, should still provide liquid and solid absorbency while preventing waste leakage. To achieve the purpose of being a replacement for conventional taped diapers, a pull-on pant should allow the wearer to raise and lower the garment without the aid of a caregiver.

Unfortunately, current pull-on pants, including wearable absorbent articles comprising reusable outer covers and disposable absorbent inserts, are not generally designed with wearer application or standing application in mind. A toilet training child or adult incontinent user may not have the dexterity, strength, or coordination to correctly don the pull-on pant. As a result, the pull-on pant may fail the wearer. The impact is that the wearer is unable to raise or lower the pull-on pant without caregiver assistance or without significant aid from the caregiver.

A further deficiency in current pull-on pant designs is that they offers no grasp point optimized for a child's or some adult incontinent user's hands. Caregivers have sufficient finger strength to apply the pull-on pant onto the wearer by pinching the pull-on pant between thumb and fingers and pulling the pant up and over the wearer's hips into a suitable position. Children and some adult incontinent wearers, however, may not have such finger dexterity, strength, and/or coordination to grasp and pull the pant up and over their own hips. When attempting to self-apply a pull-on pant, the child or adult incontinence wearer may be either unable to apply the pant or the pant may not pulled high enough onto the waist to provide effective waste absorption and control. Again, the pull-on pant may fail the wearer because the wearer is unable to raise or lower the pull-on pant without caregiver assistance. Additionally, application by caregivers to standing wearers may be complicated by the wearer's size or geometry, high coefficients of friction between the skin and the pant (e.g., for damp skin), or wearer motion or non-compliance. The pull-on pant may fail the caregiver in these instances because the caregiver is unable to raise or lower the pull-on pant in a reasonable amount of time or with acceptable results.

Furthermore, current pull-on pants provide no grasp point for caregivers or wearers to perform a finishing adjustment. This finishing adjustment, or "finish," refers to a final adjustment of the pant to ensure a proper and snug fit. Often, the finish is performed by the caregiver to ensure that the wearer has applied the pull-on pant correctly. Children and some adult incontinence wearers often have problems drawing the waistband of the pull-on pant up and over their buttocks and need the assistance of a caregiver. In such an instance, the caregiver may have difficulty grasping the pull-on pant, which may have been twisted or bunched by the wearer. Furthermore, grasping a partially applied pull-on pant may lead to uncomfortable chafing, binding, and pinching of the wearer.

In view of the foregoing, the present disclosure provides reusable outer covers configured to be engaged with disposable absorbent inserts and that comprise grasping aids to aid in the application of the pull-on pant by either a wearer or a caregiver.

SUMMARY

In an embodiment, the present disclosure is directed, in part, to a pull-on wearable absorbent article comprising a reusable outer cover comprising a grasping aid and a disposable absorbent insert. The reusable outer cover may comprise a front waist region, a rear waist region, a crotch region disposed intermediate the front waist region and the rear waist region, and a wearer-facing surface. The wearer-facing surface of the front waist region and/or the rear waist region may comprise an insert fastener component. The grasping aid may be configured to assist in the application of the article onto a wearer and may be attached to, formed with, and/or formed in the reusable outer cover. The disposable absorbent insert may comprise a forward region, a rearward region, and a crotch region disposed intermediate the forward region and the rearward region. The forward region, the rearward region, and/or the crotch region may comprise a fastener component configured to engage the insert fastener component to attach the insert to the reusable outer cover.

In an embodiment, the present disclosure is directed, in part, to a pull-on wearable absorbent article. The pull-on wearable absorbent article comprises a reusable outer cover comprising a grasping aid and a disposable absorbent insert. The reusable outer cover may comprise a front waist region, a rear waist region, a crotch region disposed intermediate the front waist region and the rear waist region, and a wearer-facing surface. The wearer-facing surface of the front waist region and/or the rear waist region may comprise an insert fastener component. The reusable outer cover may further comprise a reduced elongation zone. The grasping aid may be configured to assist in the application of the article onto a wearer and may be force-coupled to the reduced elongation zone or to another portion of the reusable outer cover. The disposable absorbent insert may comprise a forward region, a rearward region, and a crotch region disposed intermediate the forward region and the rearward region. The forward region, the rearward region, and/or the crotch region may comprise a fastener component configured to engage the insert fastener component to attach the insert to the reusable outer cover.

In an embodiment, the present disclosure is directed, in part, to a reusable outer cover configured for use with a disposable absorbent insert. The reusable outer cover and the disposable absorbent article together form a wearable absorbent article. The reusable outer cover may be configured as a pull-on pant and may comprise a front waist region, a rear waist region, a crotch region disposed intermediate the front waist region and the rear waist region, and a wearer-facing surface. The wearer-facing surface of the front waist region and/or the rear waist region may comprise an insert fastener component. The reusable outer cover may further comprise a grasping aid configured to assist in the application of the article onto a wearer. The grasping aid may be force-coupled to the insert fastener component or to another portion of the reusable outer cover.

BRIEF DESCRIPTION OF THE DRAWINGS

FIG. 1E is an illustration of a waist region of a pant having fastening zones on the sides in accordance with a non-limiting embodiment of the present disclosure;

FIG. 1F is an illustration of a waist region of a pant having fastening zones in the front waist region in accordance with a non-limiting embodiment of the present disclosure;

FIG. 1G is an illustration of a waist region of a pant having fastening zones in the rear waist region in accordance with a non-limiting embodiment of the present disclosure;

FIG. 1H is an illustration of an overlap seam in a fastening zone in accordance with a non-limiting embodiment of the present disclosure;

FIG. 1I is an illustration of a butt seam in a fastening zone in accordance with a non-limiting embodiment of the present disclosure;

FIG. 6A is a perspective view of a reusable outer cover for a pull-on wearable pant comprising a grasping aid configured as a flap in accordance with a non-limiting embodiment of the present disclosure;

FIG. 6B is a cross-sectional view of a grasping aid configured as a flap and comprising a unitary construction taken along the sectional line 6-6 of FIG. 6A in accordance with a non-limiting embodiment of the present disclosure;

FIG. 6C is a cross-sectional view of a grasping aid configured as a flap and comprising a multiple layer construction taken along the sectional line 6-6 of FIG. 6A in accordance with a non-limiting embodiment of the present disclosure;

FIG. 6D is a perspective view of a reusable outer cover for a pull-on wearable pant comprising a grasping aid configured as a handle in accordance with a non-limiting embodiment of the present disclosure;

FIG. 7A is a perspective view of a reusable outer cover for a pull-on wearable pant comprising a grasping aid configured as a tab in accordance with a non-limiting embodiment of the present disclosure;

FIG. 7B is a perspective view of a reusable outer cover for a pull-on wearable pant comprising a grasping aid configured as a tab having a sinusoidal configuration in accordance with a non-limiting embodiment of the present disclosure;

FIG. 8A is a perspective view of a reusable outer cover for a pull-on wearable pant comprising a grasping aid configured as a ridge in accordance with a non-limiting embodiment of the present disclosure;

FIG. 8B is a cross-sectional view of the grasping aid configured as a ridge comprising an insert interposed between two layers taken along the sectional line 8-8 of FIG. 8A in accordance with a non-limiting embodiment of the present disclosure;

FIG. 8C is a cross-sectional view of the grasping aid configured as a ridge comprising an insert interposed between one layer taken along the sectional line 8-8 of FIG. 8A in accordance with a non-limiting embodiment of the present disclosure;

FIG. 8D is an example cross-sectional view of a grasping aid configured as a ridge and comprising a cap along a waist edge of the pull-on pant in accordance with a non-limiting embodiment of the present disclosure;

FIGS. 9A and 9B are perspective views of a reusable outer cover for pull-on wearable pants comprising a grasping aid configured as a textured zone with an improved grippable surface in accordance with various non-limiting embodiments of the present disclosure;

FIG. 10 is a perspective view of a reusable outer cover for a pull-on wearable pant comprising a grasping aid configured as a loop in accordance with a non-limiting embodiment of the present disclosure;

FIG. 15A is an example cross-sectional view of a portion of a waist edge of a reusable outer cover having a portion of a grasping aid joined to an inner, wearer-facing surface in accordance with a non-limiting embodiment of the present disclosure;

FIG. 15B is an example cross-sectional view of a portion of a waist edge of a reusable outer cover having a portion of a grasping aid joined to an outer, garment-facing surface in accordance with a non-limiting embodiment of the present disclosure; and FIG. 15C is an example cross-sectional view of a portion of a waist edge of a reusable outer cover having a portion of a grasping aid joined to a reusable outer cover intermediate the inner, wearer-facing surface and the outer, garment-facing surface in accordance with a non-limiting embodiment of the present disclosure.

DETAILED DESCRIPTION

Definitions

Figure 1A:
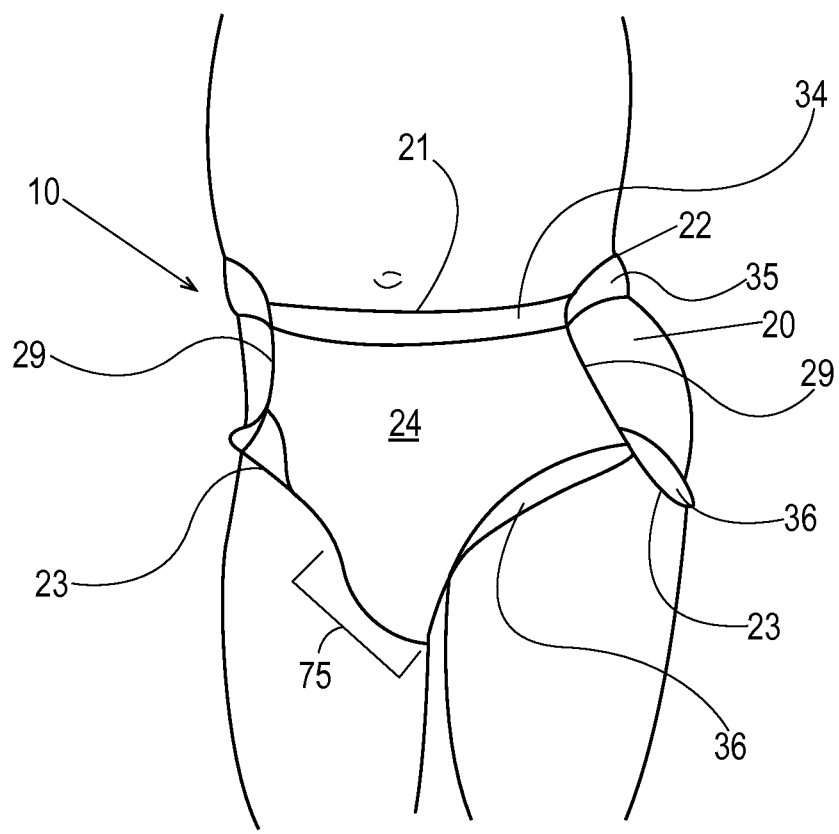
FIG. 1A is a perspective view of a wearable absorbent article as it might appear being worn by a wearer about the lower torso in accordance with a non-limiting embodiment of the present disclosure.

For purposes of this description, the following terms have the meanings set forth:

"Absorbent insert" and "insert" mean a component of a wearable absorbent article that is configured to contain and/or absorb urine, feces, menses, or any combination thereof, and is configured to be installed and removed as a modular unit, from a reusable outer cover. The insert may or may not comprise an absorbent core.

"Application" or "apply" refer to the process of donning the absorbent article on to a wearer by either the wearer or a caregiver.

"Attachment zone" means one or more fastener components positioned on or formed on the inner surface of the outer cover which are used to removably attach or join an insert to an outer cover. The fastener components of the attachment zone may be hooks, loops, adhesives, cohesive, snaps, buttons, pockets, and/or any other suitable fastener components known to one of skill in the art.

"Chassis" means a component of a wearable absorbent article that is adapted to be worn about the lower torso of a wearer, and is adapted to support an absorbent insert and hold the insert next to the wearer's body. Herein, a chassis may also be referred to as an "outer cover". The terms "outer cover" and "chassis" are interchangeable for purposes herein.

"Disposable", when referring to an absorbent insert, means that the absorbent insert is not adapted or intended to be effectively sanitarily laundered in an ordinary household laundering process and ordinary household equipment, and thereby is ordinarily unsuitable for sanitary and effective reuse so as to provide as-new intended functions and performance, following soiling by exudates and removal from an outer cover. By way of non-limiting examples, effective laundering may be frustrated or prevented, causing the insert to be disposable, by inclusion of materials and/or construction: that do not retain their substantial as-new physical shape or structure through ordinary household laundering and drying so as to be effective as-new in reuse; that absorb aqueous liquids and cannot be sufficiently dried/dehydrated in ordinary household drying equipment and ordinary drying cycles so as to be effective as-new in reuse; that dissolve or substantially degrade in ordinary household laundering or drying, causing the insert to be substantially damaged or rendered useless; and/or that cannot be effectively cleaned of exudate material through ordinary laundering, so as to be sanitary and otherwise acceptable for re-use.

"Fastening zone" means an area of fastening, attachment, or joining of a portion of an outer cover (e.g., a portion in a front waist region) to another portion of the outer cover (e.g., a portion in a rear waist region) to form a seam. The fastening, attachment, or joining, may be permanent, releasable, or refastenable. The fastening zones may each form a seam, such as an overlap seam or a butt seam, configured to join a portion of a front waist region to a portion of a rear waist region. An outer cover may comprise one or more fastening zones. Each portion of each fastening zones described herein may extend, at least in part, in the longitudinal direction (i.e., parallel to the longitudinal axis of the outer cover) or in generally the longitudinal direction (e.g., +/−20 degrees from the longitudinal axis). Each portion of each fastening zone may also extend in the lateral direction or in generally the lateral direction.

"Finishing adjustment" or "finish," when used in reference to applying the wearable absorbent article, refers to a final adjustment of the wearable absorbent article to ensure a proper (i.e., the article is not creased, pinched, inverted, twisted, etc.) and snug fit. Often, although not exclusively, the finish is performed by the caregiver. The finish may include drawing the wearable absorbent article over the wearer's buttocks and to the wearer's waist.

"Joined" and "attached" encompass configurations whereby an element is directly secured to another element by affixing the element directly to the other element and configurations whereby an element is indirectly secured to another element by affixing the element to intermediate member(s), which in turn are affixed to the other element.

"Lateral" (and forms thereof), with respect to a wearer, means along a direction generally transverse or across the direction extending from the front to the rear of the wearer, or vice versa. With respect to a component of a wearable absorbent article, "lateral" (and forms thereof), means along a direction generally transverse, across, or perpendicular to the direction extending along the component as it would be properly situated on a wearer, from the front to the rear of the wearer, or vice versa.

"Longitudinal" (and forms thereof), with respect to a wearer, means along a direction generally extending from the front to the rear of the wearer, or vice versa. With respect to a component of a wearable absorbent article, "longitudinal" (and forms thereof), means along a direction generally extending along or parallel to the component as it would be properly situated on a wearer, from the front to the rear of the wearer, or vice versa.

"Outer cover" means a component of a wearable absorbent article that is configured to be worn about the lower torso of a wearer, and that is configured to support an insert and hold the insert next to the wearer's body. The outer cover may be attached to the insert through the use of attachment zones on the insert and attachment zones on the insert. The outer cover may form a pant or may be configured to form a pant by attaching or joining portions of the fastening zones together. Herein, an outer cover may also be referred to as a "chassis". The terms "outer cover" and "chassis" are interchangeable for purposes herein, and include, but are not limited to, garments having features as described herein and configured as diapers, diaper covers, underpants, briefs, training pants, boxer shorts, pants, and/shorts, for example.

"Pant" or "Pull on Pant" means a wearable absorbent article having a continuous perimeter waist opening and continuous perimeter leg openings in an outer cover thereof designed for infant, child, or adult wearers (i.e., adult incontinence). A pant may be configured with a continuous or closed waist opening and at least one or two continuous, closed, leg openings prior to the article being applied to the wearer. A pant may be preformed (e.g., by a manufacturer or a user) by various techniques including, but not limited to, joining together portions of fastening zones of an outer cover or using any refastenable and/or permanent closure member (e.g., seams, heat bonds, pressure welds, adhesives, cohesive bonds, mechanical fasteners, etc.). A pant may be preformed anywhere along the circumference of the wearable absorbent article in the waist region (e.g., side fastened or seamed, front waist fastened or seamed, rear waist fastened or seamed). A pant may be opened about one or both of the seams and then refastened and/or readjusted. Pants having fasteners in fastening zones of the outer cover that form the circumference may be joined at the sides, in the front waist region, and/or in the rear waist region. A pant is formed by a reusable outer cover and a disposable absorbent insert, when the disposable absorbent insert is joined with the reusable outer cover. To be classified as a pant, the absorbent article should be designed such that when in a closed configuration (i.e., the waist and leg openings have a continuous circumference), the pant may be pulled up over the wearer's thighs and buttocks to the waist. Pants should have sufficient stretch and/or extension to enable such pulling up over the thighs and buttocks all while not having such a wide waist such that the pant falls down on smaller wearers once pulled up. These features, among others, differentiate pants from and taped diapers that are wrapped around the wearer when the wearer is lying down and not "pulled up". In some embodiments, the pant, when in an open (or partially open (e.g., one closed leg opening)) configuration, may be applied to a standing wearer.

"Reusable", when referring to an outer cover, means an outer cover that is configured to permit removal of at least a first insert, and replacement thereof with at least a second insert, without substantial destruction of any components of the outer cover that are necessary to provide the substantial as-new functionality of the outer cover, and without the necessity of any repair or reconstruction following such insert replacement.

"Self-application" or "self-apply" refer to the process of donning the wearable absorbent article onto a wearer by the wearer.

"Taped diaper" means a wearable absorbent article comprising an outer cover having an initial front waist region and an initial rear waist region that are not fastened, pre-fastened, or connected to each other, prior to being applied to the wearer. The taped diaper may also include an insert joined to the outer cover through the use of attachment zones on the outer cover and the insert. A taped diaper may be folded about its lateral central axis with the interior of one waist region in surface to surface contact with the interior of the opposing waist region without fastening or joining the waist regions together.

"Use," with respect to an outer cover, means one event of the wearing of the outer cover until the time an insert is replaced.

"User" means a caregiver or other person who may apply a wearable absorbent article to a wearer. Where the wearer is capable of donning the wearable absorbent article him/herself, the wearer is also a "user".

"Wearer" means a person who may wear the wearable absorbent article described herein.

In various embodiments, the present disclosure provides various ergonomic grasping aids configured to enable a wearer or caregiver to more easily don a pull-on wearable absorbent article, such as a pull-on pant comprising a reusable outer cover and a disposable absorbent insert. The pull-on pant may be for a wearer of any size or age. The grasping aids may take on any suitable configurations, such as the configurations discussed in greater detail below, for example. Before beginning to discuss the example grasping aids of the present disclosure, various details of the pull-on wearable absorbent articles comprising reusable outer covers and disposable absorbent inserts will be discussed.

Two-Piece Wearable Absorbent Articles

In an embodiment, FIG. 1A depicts an example of a wearable absorbent article 10 that is a pant positioned about a lower torso of a wearer. The pant comprises a reusable outer cover or outer cover 20 having a front waist edge 21, a rear waist edge 22, leg opening edges 23, fastening ears 29, and leg bands. The outer cover comprises an inner, wearer-facing surface 25 (not illustrated in FIG. 1A) and outer, garment-facing surface 24. The outer cover 20 may be configured to receive an insert as discussed in further detail below. The fastening ears 29 may be used to permanently or refastenably join the rear waist region to the front waist region or vice versa to form the pant. In an embodiment, one of the fastening ears 29 may be permanently joined to the front waist region, while the other fastening ear 29 may be releasably joined to the front waist region. In an embodiment, the fastening ears 29 may be positioned on the front waist region and be permanently or refastenably joined to the rear waist region to form the pant. The pant may also comprise a pouch-like structure 75 in a crotch region thereof.

Figure 1B:
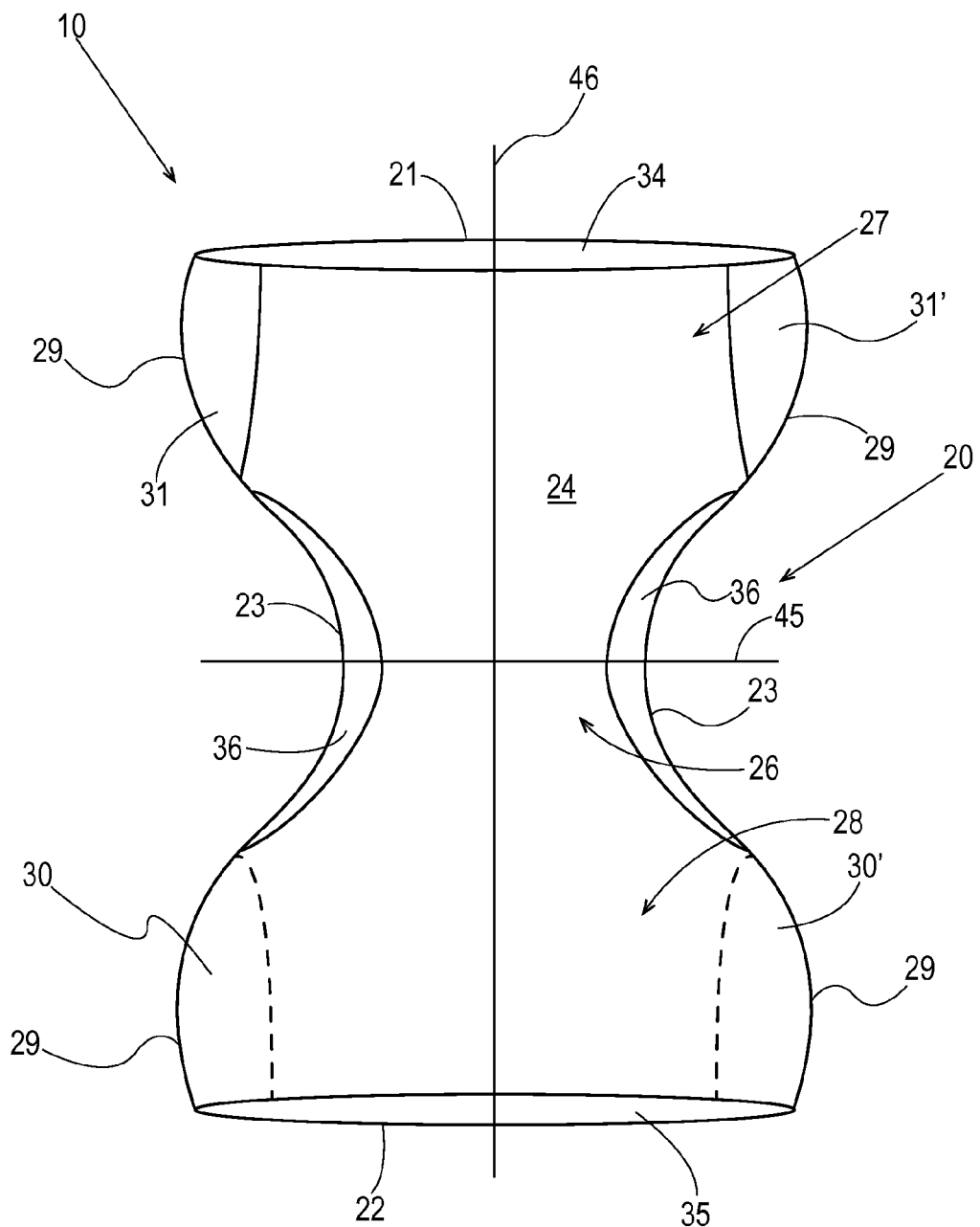
FIG. 1B is a plan view of an outer cover of FIG. 1A opened and laid flat, outer surface facing (i.e., garment-facing surface) the viewer in accordance with a non-limiting embodiment of the present disclosure.
Figure 1D:
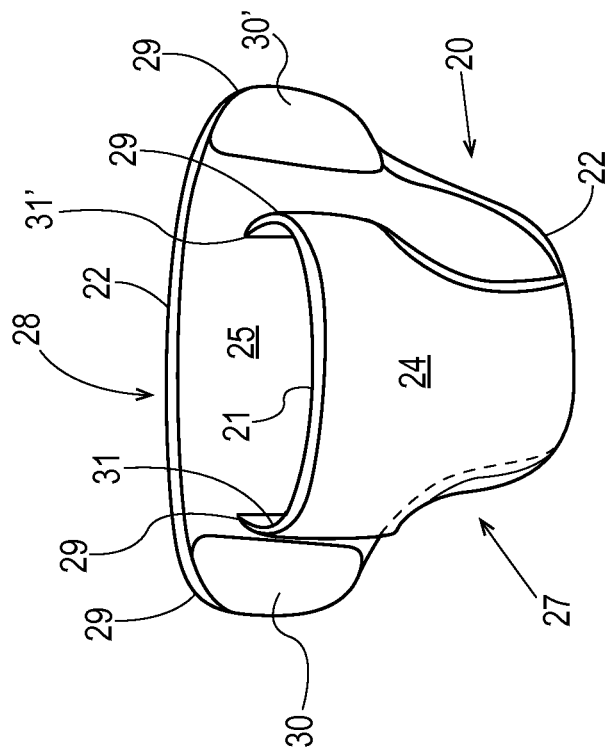
FIG. 1D is a perspective view of the wearable absorbent article of FIG. 1C with the fastening zones in an open configuration in accordance with a non-limiting embodiment of the present disclosure.
Figure 1C:
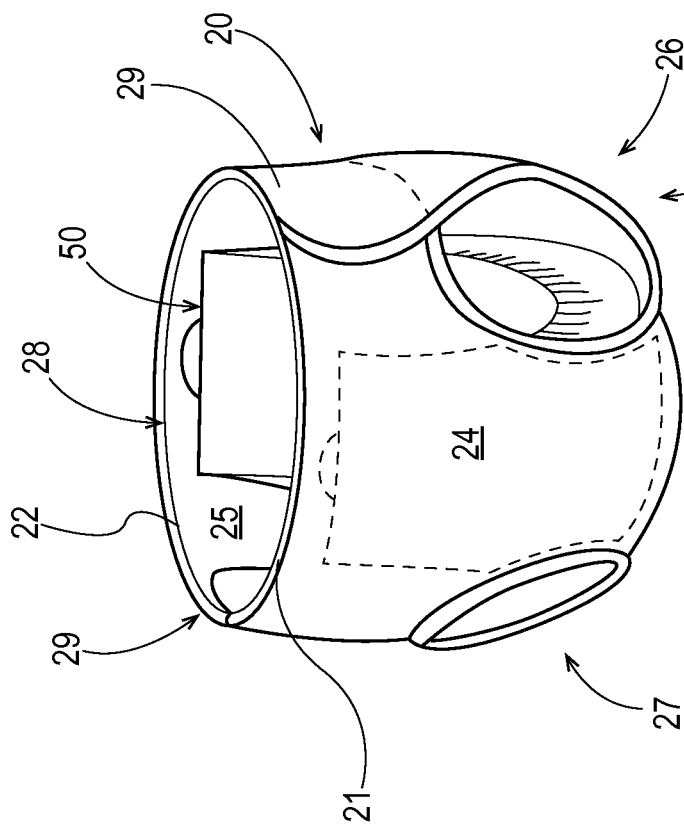
FIG. 1C is a perspective view of a wearable absorbent article with the fastening zones in a closed configuration and with a disposable absorbent insert positioned therein in accordance with a non-limiting embodiment of the present disclosure.

FIG. 1B illustrates the outer cover 20 of the pant as it may appear open and laid flat. In FIG. 1B, the outer surface 24 faces the viewer. The outer cover 20 may comprise a front waist region 27, a crotch region 26, and a rear waist region 28. The front waist region 27 may be positioned on a first side of a lateral axis 45 and the rear waist region 28 may be positioned on a second side of the lateral axis 45. The crotch region 26 may extend across the lateral axis 45 such that a portion of the crotch region 26 is positioned on a first side of the lateral axis and a second portion of the crotch region 26 is positioned on a second side of the lateral axis. The outer cover 20 may comprise a front waist band 34, a rear waist band 35, and a longitudinal axis 46. FIG. 1C illustrates an outer cover 20 with an insert 50 positioned therein and attached thereto. In FIG. 1C the fastening ears 29 have been joined. FIG. 1D illustrates the outer cover 20 of FIG. 1C without the insert 50 and with the fastening ears 29 unjoined.

FIG. 1E is an illustration of a top view of a pant having fastening zones positioned on the side of the pant. FIG. 1F is an illustration of a top view of a pant having fastening zones positioned toward the front of the pant. FIG. 1G is an illustration of a top view of a pant having fastening zone positioned toward the rear of the pant. It will be understood that each embodiment disclosed herein may have fastening zones or seams at the side, in the front, or in the rear of the pant, although not specifically illustrated for each particular embodiment.

Any of the fastening zones of the present disclosure may create overlap seams (FIG. 1H) or butt seams (FIG. 1I). Other seams known to those of skill in the art may also be provided.

Figure 2A:
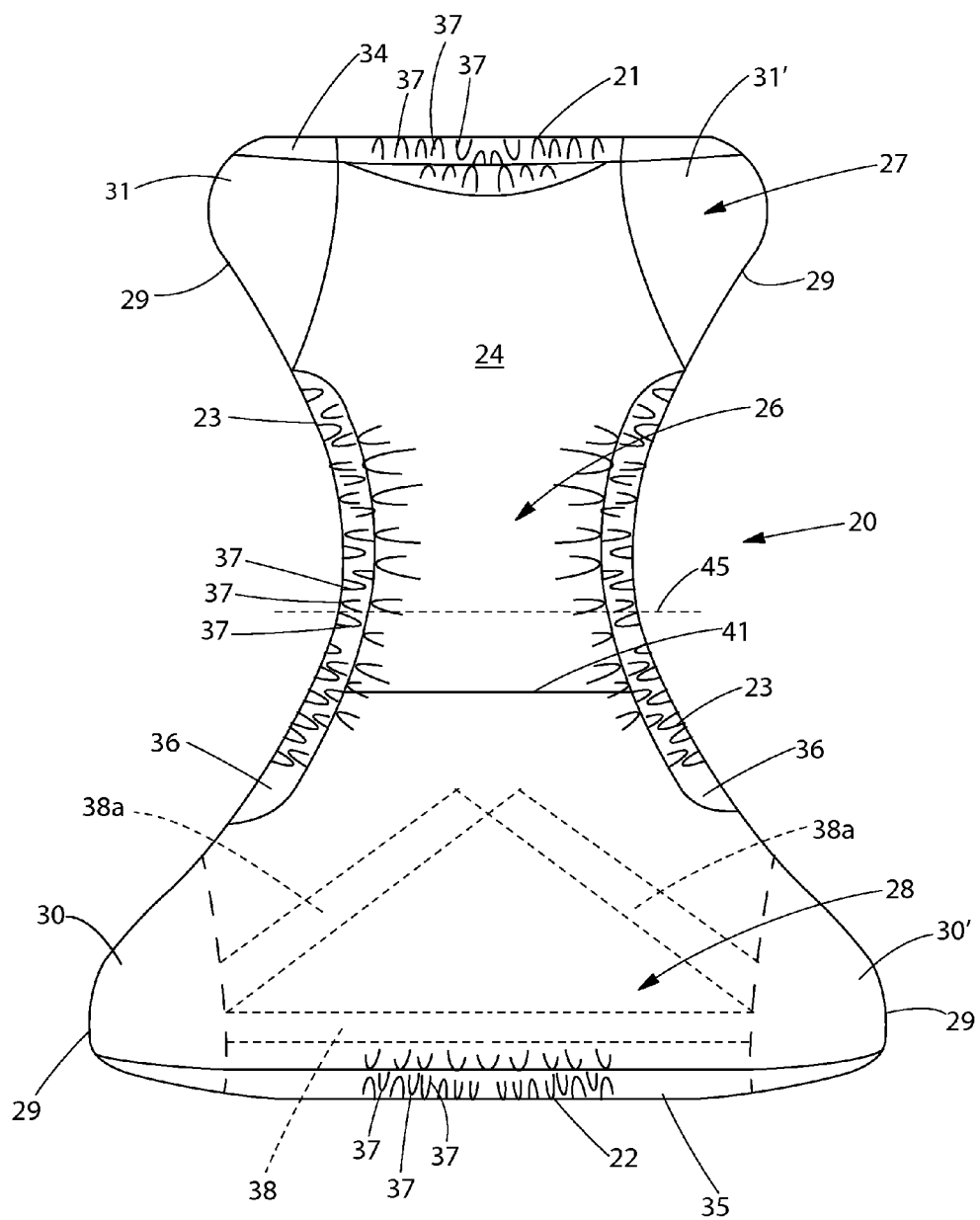
FIG. 2A is a plan view of an outer cover opened and laid flat, outer surface facing the viewer in accordance with a non-limiting embodiment of the present disclosure.
Figure 2B:
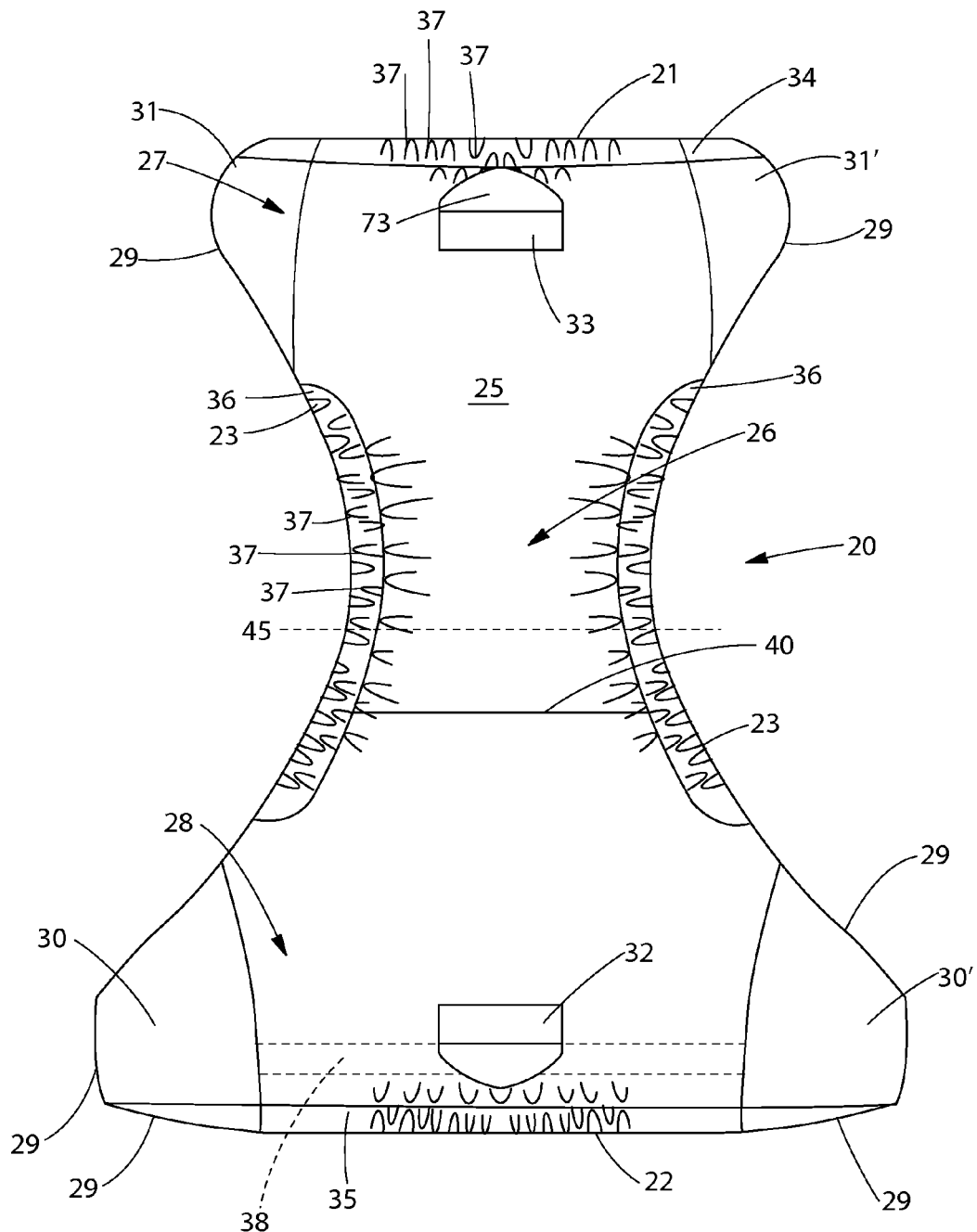
FIG. 2B is a plan view of an outer cover opened and laid flat, inner surface (i.e., wearer-facing surface) facing the viewer in accordance with a non-limiting embodiment of the present disclosure.
Figure 2C:
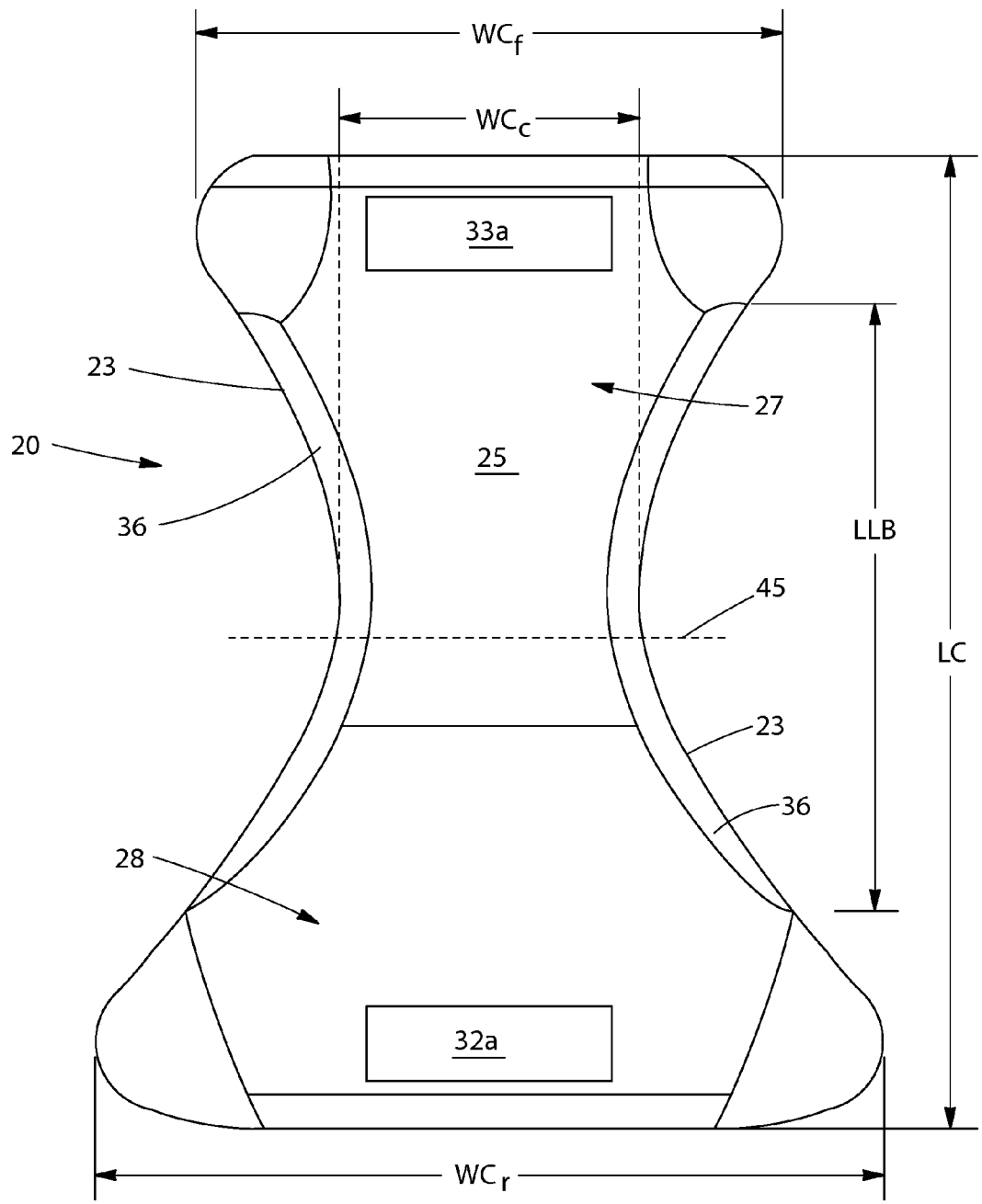
FIG. 2C is a plan view of an outer cover opened and laid flat, inner surface facing the viewer in accordance with a non-limiting embodiment of the present disclosure.

In some embodiments, FIGS. 2A, 2B and 2C depict an outer cover 20 of the present disclosure as it may appear opened and laid flat. In FIG. 2A, the outer, garment-facing surface of outer cover 20 face the viewer, while in FIGS. 2B and 2C, the inner, wearer-facing surfaces of outer cover 20 face the viewer. The front and rear waist edges 21, 22 are depicted at the top and bottom of the drawings, respectively. The outer covers 20 may have a crotch region 26, a front waist region 27, a rear waist region 28, and pairs of fastening ears 29 laterally extending from the rear waist region 28 and the front waist region 27. Each of the fastening ears 29 may comprise a side of a fastening zone (31 and 30 when joined together form a fastening zone and 31' and 30' when joined together form a fastening zone). The fastening zone 31 and 30 or first fastening zone and the fastening zone 31' and 30' or second fastening may be may be engaged with each other to join the front waist region 27 to the rear waist region 28. The first fastening zone is on a first second of the longitudinal axis and the second fastening zone is on a second side of the longitudinal axis.

Referring to FIG. 2C, the outer cover 20 may have a length LC from the forwardmost portion of the front waist edge 21 to the rearwardmost portion of the rear waist edge 22, and an outer cover lateral axis 45 equally dividing this length. Thus, the front waist region 27 may be positioned on a first side of the outer cover lateral axis 45 and the rear waist region 28 may be positioned on a second side of the outer cover lateral axis 45. The crotch region 26 may be positioned on the first side of the outer cover lateral axis 45 and on the second side of the outer cover lateral axis 45. The outer cover 20 may have disposed thereon one or more attachment zones such as front and rear attachment zones 33, 33a and 32, 32a for attachment of an insert to the outer cover 20. Other configurations of front and rear attachment zones are also contemplated although not illustrated in the figures for brevity.

Figure 3:
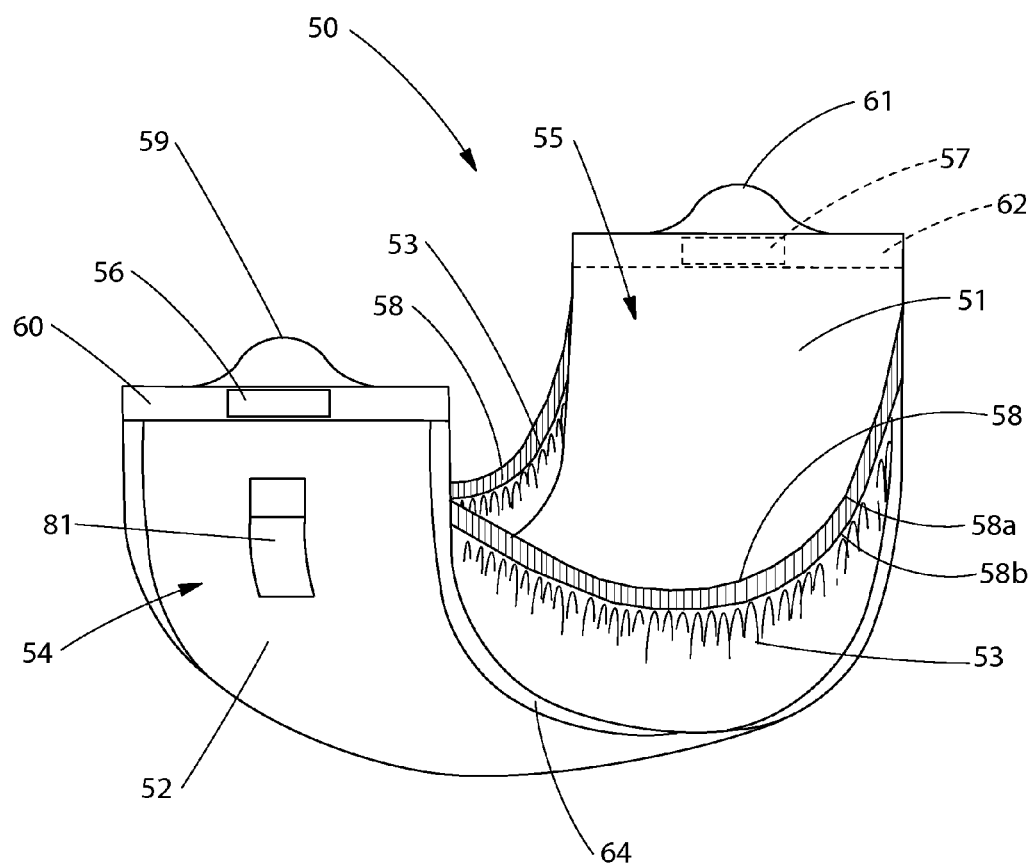
FIG. 3 is a perspective view of an insert shown apart from an outer cover, as it might appear in a free-standing, relaxed state in accordance with a non-limiting embodiment of the present disclosure.
Figure 4:
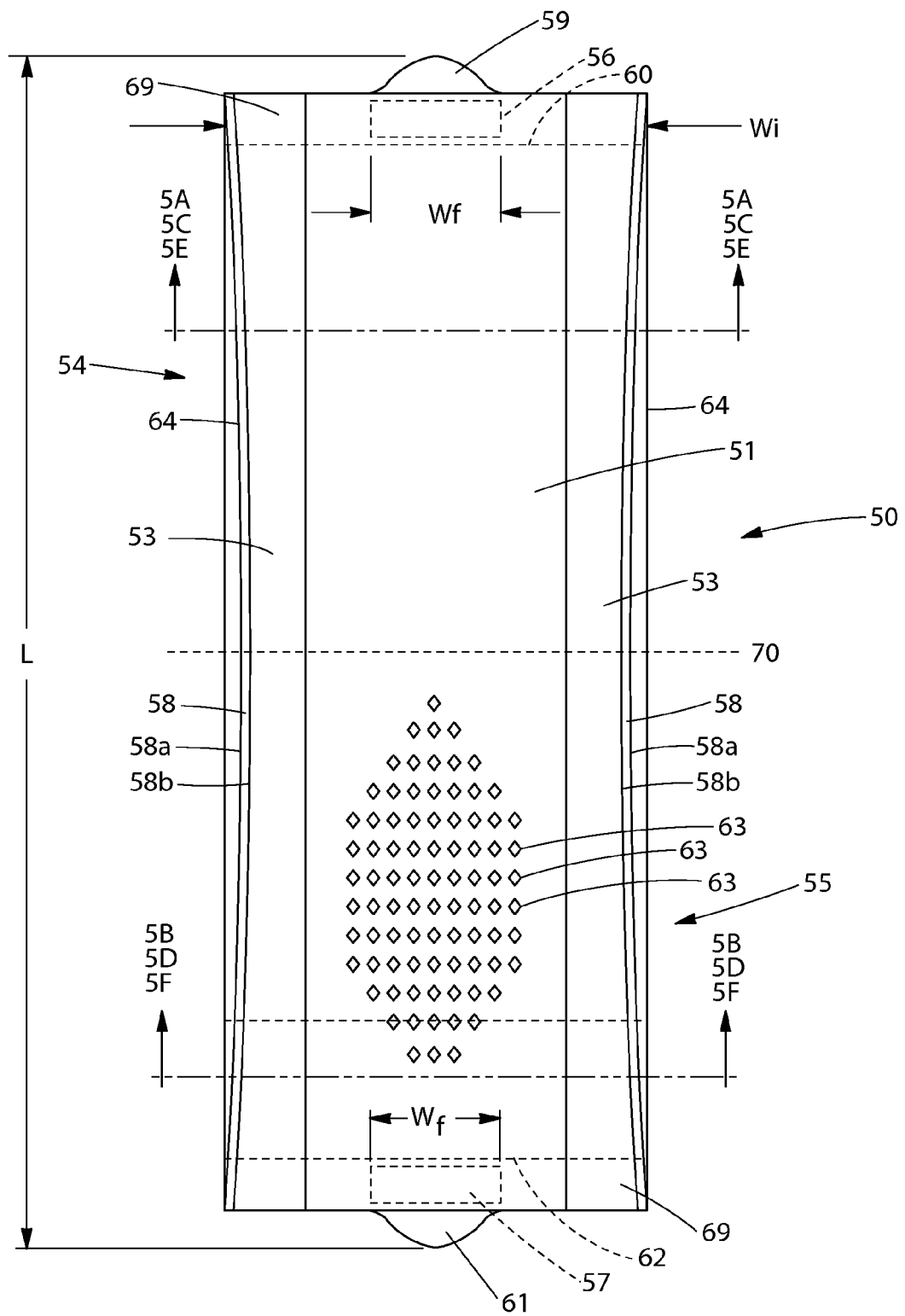
FIG. 4 is a plan view of an insert shown stretched out and laid flat, inner surface facing the viewer in accordance with a non-limiting embodiment of the present disclosure.

FIG. 3 depicts a disposable absorbent insert 50 that may form an inner component of the wearable absorbent article 10, shown in perspective view as it might appear in a free-standing, relaxed state, apart from the outer cover 20. The insert 50 may be designed to contain and/or absorb body exudates, and may be made of pliable materials as will be described further below. The insert 10 may have forward region 54 and rearward region 55, and may include one or more front fastener components 56 and one or more rear fastener components 57 configured to engage the front and rear attachment zones 33 and 32 on the outer cover 20. The insert 10 may include a body-facing liner or topsheet 51, an outer liner or backsheet 52, and a pair of standing cuffs 53. Referring to FIG. 4, the insert 50, when fully opened and laid flat, may have a length L from the forwardmost portion of the forward region 54 to the rearwardmost portion of the rearward region 55, and an insert lateral axis 70 equally dividing this length. Thus, the forward region 54 is positioned on a first side of the insert lateral axis 70 and rearward region 55 may be positioned on a second side of the insert lateral axis 70.

In an embodiment, referring to FIGS. 2B and 3, the insert 50 may have rear fastener component 57 disposed thereon. Alternatively, or in addition, the outer cover 20 may have rear insert fastener component 32 disposed thereon. Similarly, the insert 50 may have front fastener component 56 disposed thereon. Alternatively, or in addition, the outer cover 20 may have front insert fastener component 33 disposed thereon. If a two-component fastening system is used, fastener component pairs 57, 32 and 56, 33 may be cooperating components that affect fastening therebetween when these respective components are brought together. Thus, in the example depicted, in order to install the absorbent insert 50 into the outer cover 20, a user may lay the outer cover 20 flat, inner surface 25 facing up, stretch and orient the insert 50 such that the rear fastener component 57 faces the rear insert fastener component 32 and the front fastener component 56 faces the front insert fastener component 33, and bring these respective fastener component pairs 57, 32 and 56, 33 together to effect fastening therebetween. In other embodiments, the user may position the insert 50 into a closed waist circumference pant, by folding the insert about the lateral axis 46, inserting the insert 50 into and at least partially through the closed waist circumference of the outer cover 20, and bringing the respective fastener component pairs 57,32, and 56, 33 together.

If it is desired that the outer cover 20 be reusable, for the outer cover 20 to remain substantially sanitary and useful (without requiring laundering or disposal) after removal and replacement of an insert, it may be desired that all parts of the outer cover 20 remain substantially unsoiled after an exudation of waste (especially fecal matter) by the wearer. Thus, it may be desired that when the insert 50 is installed within an outer cover 20, there is no non-removable portion or component of the outer cover 20 that lies over or covers a substantial portion of wearer-facing surfaces of the insert 50. Stated another way, no non-removable portion or component of the outer cover 20 is situated between a substantial portion of the insert 50 and the wearer when the wearable absorbent article 10 is worn, at least in the areas proximate to wearer body features that discharge exudates. Thus, it may be desired that the outer cover 20 include no non-removable cover sheet or the like that covers or contains substantial portions of wearer-facing surfaces of the insert 50 within the outer cover 20, nor any overlying structures such as pockets, straps or flaps that substantially wrap or cover the insert proximate to exudate discharge points, or lie substantially between the insert 50 and the wearer's anus and/or genitals, when the wearable absorbent article 10 is worn. If the outer cover 20 lacks such overlying structures, this may increase the likelihood that the wearer's exudates will contact only the insert 50, and not portions of the outer cover 20.

Referring to FIGS. 1A, 2A and 2B, it can be seen that the wearable absorbent article 10 may be placed on a wearer by attaching the insert 50 to the outer cover 20, attaching the fastening zones 30 and 31 and 30' and 31 to form a pant, and pulling the pant up the legs and over the thighs, hips, and buttock into the position illustrated in FIG. 1A. In an embodiment, the outer cover 20 may come from a manufacturer in a pre-formed state (i.e., continuous waist and leg perimeters) having permanent or refastenable seams, for example. In such an instance, the insert 50 may be inserted into the outer cover 20 and then pulled up the legs, over the thighs, hips, and buttocks into position on a wearer. When the insert 50 has been installed into the outer cover 20, the insert 50 may then be disposed within the outer cover 20, next to the wearer, with the standing cuffs 53 oriented and extending longitudinally adjacent the inner portions of leg edges 23 (i.e., longitudinally between the wearer's legs).

Materials

The outer cover 20 and/or layers or portions thereof may be made of any knitted, woven or nonwoven textile, film, or textile-like material that is appropriately compatible with skin of the intended wearer(s). The outer cover 20 may be constructed of durable and/or semi-durable materials. Generally, only for purposes of reference in this description, "durable" refers to a woven or knitted textile material of any kind that may be used as a component of a washable clothing article. As used herein, "durable" includes materials which are "launderable" as defined and described in co-pending U.S. Patent Application Publication Nos. 2010/0179495, 2010/0179503, and 2011/0172628, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on Jan. 14, 2010. Generally, only for purposes of this description, "semi-durable" refers to a nonwoven material or laminate thereof that when used as an outer cover material can withstand more than one use with an insert without losing its structural integrity to an extent that renders it unserviceable. As used herein, "semi-durable" includes materials which are "laundering resistant" as defined and described in the U.S. applications identified immediately above. Thus, the outer cover 20 may be constructed of materials and construction that make it reusable and/or washable.

The durable materials of which the outer cover 20 may be constructed may include any natural or synthetic textile materials known in the diaper, pant, underwear, performance clothing, sport clothing, or general clothing or textile arts. The durable materials may include woven or knitted textiles made of natural fibers such as cotton, linen, wool, bamboo, hemp, silk, and/or rayon, for example, as well as blends of any of these fibers with any other(s), or with synthetic fibers. Examples of synthetic fibers suitable for use as components of the durable materials include polyester, nylon, spandex and/or other elastomer fibers.

Semi-durable outer cover materials may include any natural or synthetic nonwoven web and/or film materials known in the diaper or pant arts. Semi-durable materials of which the outer cover 20 may be constructed may include non-woven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of the outer cover 20.

The outer cover 20 also, or additionally, may include a laminated or substantially separate film layer, which may be elastic, to provide enhanced liquid penetration resistance and/or elastic properties.

The outer cover 20 may be formed of a single layer of a durable or semi-durable material, or may have two or more layers in the front waist region 27, the rear waist region 28, the crotch region 26, and the leg openings. Accordingly, referring to FIG. 2B, an example inner surface 25 may be formed by a second layer of a durable or semi-durable material. The material selected may include fibers having hydrophobic properties, providing enhanced liquid containment attributes to the second layer. In another example, however, it may be desirable in some circumstances for the selected material to include hydrophilic fibers, or fibers treated to be hydrophilic. This may be desired in some circumstances to cause the material forming the inner surface 25 to more readily absorb liquid, or transmit liquid therethrough. This may serve to provide supplemental absorbency within the outer cover for an event in which liquid exudates escape the insert 50, reducing the likelihood that the outer cover 20 will leak. Alternatively, it may provide one way of communicating to the user that liquid exudates have escaped the insert 50, by causing wetness to be transmitted through to the outer cover outer layer such that wetness is visible on outer surface 24. Alternatively, it may serve to provide a layer that tends to draw moisture away from the skin, for a drier, more comfortable feel.

Referring again to FIGS. 2A and 2B, in addition to forming differing layers of differing materials, it may be desirable to form a single layer of differing materials, for example, differing materials in the respective front, crotch, and/or rear regions B 27, 26, and 28 of the outer cover 20. Such differing materials may be joined at a seam such as an inner seam 40 (FIG. 2B) and/or outer seam 41 (FIG. 2A). In other embodiments, the two different properties may be inherent to a single piece of fabric, for example.

Elasticized Waistbands, Leg Bands

Referring again to FIGS. 1A, 2A and 2B, a front waist band portion 34, a rear waist band portion 35, and leg band portions 36 are illustrated. One or more of these band portions 34, 35, 36 may be formed of one or more strands or strips including an elastomeric material, such as spandex or a blend of spandex and other fibers, enveloped by a nonwoven or textile material, which may include the edges of the material forming the inner and/or outer layers of outer cover 20, to form and elasticize the respective band portions. Textile material(s) enveloping the elastic strand(s) or strip(s) may be sewn around elastic strand(s) or strip(s) to hold them in place within the respective band portions. If the elastic material is strained prior to, and while, being enveloped and affixed to form these band portions during the manufacturing process, upon relaxation the enveloping material and adjacent outer cover material may be caused to gather and form ruffles 37 therealong, which constitute gathered outer cover material. This can serve to promote snug fit, wearer comfort and appearance. The band portions may be disposed along the edge of the outer cover, and in some circumstances it may be desired to have the band portions situated along substantially the entire length of the leg and/or front or rear waist openings so as to form bands that substantially or completely encircle the wearer's legs and/or waist while outer cover 20 is worn. The gathered material within the ruffles 37 may serve to accommodate stretching of the waist band portions 34, 35 and the leg band portions 36.

Anchoring Bands

In an embodiment, the outer cover 20 also may include an anchoring supplement, such as anchoring band 38, disposed on or in the outer cover rear waist region 28 as indicated in FIGS. 2A, 2B. Various anchoring bands may also extend into and/or through the crotch region 26 and/or the waist regions 27 and 28. In an embodiment, one anchoring band may cross over another anchoring band. As suggested in FIGS. 2A and 2B, the anchoring band 38 may be affixed along a layer, or disposed between layers, forming the inner surface 25 and the outer surface 24 of the outer cover 20. The anchoring band 38 may include an elastomeric or elasticized strip or band of material, affixed to the outer cover 20 at locations proximate to its rearward corners or proximate to fastening ears 29. When strained laterally by application to the wearer, the anchoring band 38 may serve to provide, or supplement, lateral tensile forces in the wearable absorbent article 10 about the wearer's waist, thereby tending to draw the waist opening snug, enhancing fit and enhancing securement of the wearable absorbent article 10 about the wearer's waist. The elastic property (e.g., elastic modulus and maximum elastic extension) of the anchoring band 38 may be higher than or different than the elastic property of the surrounding, adjacent, or coextensive outer cover materials.

In another example, instead of, or in addition to, being oriented substantially laterally as suggested by the depicted location of the anchoring band 38 in FIGS. 2A and 2B, one or more members forming anchoring bands may be oriented diagonally between the longitudinal and lateral directions. For example, as suggested in FIG. 2A, a pair of diagonal anchoring bands 38a may have respective waist ends thereof affixed at a location area proximate to corners of the outer cover 20 and/or the fastening ears 29, and respectively extend toward both the lateral and longitudinal center of the outer cover 20, as suggested in FIG. 2A.

Outer Cover Asymmetry

In order to enhance and/or maximize fit, wearer comfort and appearance of the outer cover 20, it may be desirable to fashion the outer cover 20 so as to accommodate anatomical contours and body movements of the intended wearer. For example, as suggested by FIGS. 2A and 2B, the outer cover 20 may have differing shape and/or greater material surface area in the rear waist region 28 than in the front waist region 27. Human anatomy in the lower torso/hip/thigh region is asymmetric about the lateral plane of the body, i.e., the geometry of the front of the human body is different than that of the back. To provide for better fit and comfort, the outer cover geometry and functionality, including stretch properties, may be adapted accordingly. Differing shape and/or greater material surface area in the rear waist region 28 may serve to better cover the buttocks through movements of the wearer (including sitting and/or bending forward at the hips), while lesser material surface area in the front waist region 27 may serve to avoid material bunching and/or an ill-fitting appearance, particularly when the wearer is in positions including sitting and/or bending forward at the hips. As a result, the outer cover 20 may be asymmetric in shape or surface area across the outer cover lateral axis 45.

For purposes of this description, when used with respect to an outer cover 20, "asymmetric" and "asymmetry" mean that features, geometry (e.g., shape), materials and/or construction on one side of the outer cover lateral axis 45 differ substantially in some respect from those on the other side of the outer cover lateral axis 45. Such asymmetric construction results from having various features of the outer cover 20 designed to accommodate the body features and functions of the intended wearer as they differ front-to-rear, to enhance containment/absorbency performance, comfort, fit and/or appearance of the wearable absorbent article, and/or to economize on use of materials. "Asymmetric" and "asymmetry" do not refer to differences across the outer cover lateral axis 45 that are attributable to features that may be included on an outer cover 20 only for purposes of: purely cosmetic coloration or surface decoration; fastening an insert (such as fastening zones described herein); bundling, folding, storing or carrying the outer cover; indicia for orienting an insert within an outer cover 20 or vice versa (such as orientation indicia described herein), or for other purposes substantially unrelated to the body features and functions of the intended wearer as they differ front-to-rear, to affect performance, comfort, fit, and/or physical appearance of the wearable absorbent article 10, and/or to economize on use of materials.

Examples of Possible Disposable Absorbent Insert Details

Examples of features of an absorbent insert 50 will be described with reference to FIGS. 3, 4, and 5A-F. The present disclosure also contemplates the use of other inserts with other features and is not limited to the inserts described below.

As noted above, FIG. 3 depicts a disposable absorbent insert 50 that may form an inner component of a wearable absorbent article 10 as described herein, shown in perspective view as it might appear in a free-standing, relaxed state, apart from an outer cover 20. FIG. 4 depicts an example of an absorbent insert 50 shown stretched out and laid flat (against elastic-induced contraction to a position similar to that shown in FIG. 3), wearer-facing surfaces facing the viewer. FIGS. 5A-5F depict cross sectional views of an insert 50 as indicated in FIG. 4, in various possible examples.

The insert 50 may have a topsheet 51 and a backsheet 52 forming an envelope-like enclosure for absorbent core materials such as those described further below. The topsheet 51 and the backsheet 52 may be affixed together along longitudinal seams 64, and along lateral seams 69. The insert 50 also may have longitudinal standing cuffs 53 affixed therealong.

Topsheet

The topsheet 51 may be formed of a liquid-permeable nonwoven web material. It may be desired that the material forming the topsheet 51 is compliant, soft-feeling, and non-irritating to the wearer's skin. It may be desired that at least a portion of the topsheet 51 may be liquid pervious, permitting liquids to readily penetrate through its thickness. A suitable topsheet may be manufactured from a wide range of materials, such as porous foams, reticulated foams, apertured plastic films, apertured nonwoven materials, or woven or nonwoven materials of natural fibers (e.g., wood or cotton fibers), synthetic fibers (e.g., polyester or polypropylene fibers), or a combination of natural and synthetic fibers. If the topsheet 51 includes fibers, the fibers may be spunbond, carded, wet-laid, meltblown, hydroentangled, or otherwise processed as is known to those of skill in the art. Any suitable topsheets known to those of skill in the art may be used with the inserts of the present disclosure.

Backsheet

The backsheet 52 is generally that outer liner portion of the insert 50 forming the garment-facing surface thereof, and prevents, or at least inhibits, the exudates absorbed and contained within the insert 50 from wicking through and soiling the outer cover 20. In some circumstances it may be desired that the backsheet 52 is substantially impervious to liquids.

Any suitable backsheets known to those of skill in the art may be used with the inserts of the present disclosure.

Absorbent Core

In an embodiment, referring to FIGS. 5A-F, the insert 50 may have an absorbent core 71 within the envelope-like structure formed by the topsheet 51 and the backsheet 52. The absorbent core 71 may comprise any absorbent material which is generally compressible, conformable, non-irritating to the wearer's skin, and capable of absorbing and retaining liquids, such as urine and other certain body exudates. The absorbent core 71 may comprise a wide variety of liquid-absorbent materials commonly used in disposable diapers and other absorbent articles such as comminuted wood pulp, which is generally referred to as airfelt and/or superabsorbent polymers.

The absorbent core 71 may include liquid acquisition/distribution material 65, and storage material 66. Generally, acquisition/distribution material 65 may have comparatively rapid absorption and wicking properties, but also may have limited absorption capacity. Conversely, generally, the storage material 66 may have comparatively slower absorption and wicking properties, but also may have greater absorption capacity. Thus, the acquisition/distribution material 65 may serve to rapidly absorb and distribute gushes of liquid such as urine, while the storage material 66, having greater absorption capacity, may serve to absorb such liquid from the acquisition/distribution material and store it for the time needed until the insert 50 may be replaced.

Standing Cuffs

The insert 50 also may have a pair of longitudinal standing cuffs 53 attached partially or entirely along the longitudinal length thereof. Suitable longitudinal standing cuffs (in various published examples identified as "leg cuffs", "barrier cuffs" "gasketing cuffs," etc., may be formed of materials and construction such as described in, but not limited to, U.S. Pat. Nos. 6,786,895; 6,420,627; 5,911,713; 5,906,603; 5,769,838; 5,624,425; 5,021,051 and 4,597,760; and U.S. Patent Application Publication No. 2007/0239130 and U.S. Pat. No. 8,002,760. As shown in FIG. 3, the standing cuffs 53 may have one or more strands or strips of cuff elastics 58*a*, 58*b* disposed longitudinally therealong. If such cuff elastics 58*a*, 58*b* are pre-strained prior to being affixed to the web material forming the standing cuffs 53, resulting longitudinal tensile forces therealong may cause the web material forming the standing cuffs 53 to gather as shown, and cause the cuffs 53 to extend from the body of the insert 50 (upwardly relative to FIG. 3), or causing them to "stand". This feature causes the standing cuffs 53 to form a gasketing structure along the wearer's body when the wearable absorbent article 10 including the insert 50 is worn, longitudinally on either side of the anatomical features where waste is exuded. Thus, the standing cuffs 53 may serve to enhance the exudate containment capability of the insert 50 and, and as a result, of the wearable absorbent article 10. As with the backsheet 52, the standing cuffs 53 may be formed of a substantially liquid impermeable web so as to contain and isolate liquid exudates from the outer cover 20, outer clothing and environment of the wearer. At the same time, the standing cuffs 53 may be vapor permeable to provide for breathability of the insert 50 and the wearable absorbent article 10, reducing humidity in the areas between the insert and the wearer's body, and helping reduce the likelihood of skin irritation and/or rashes that may result from over-hydration of the skin. In another example, the material forming the standing cuffs 53 may be integral with the material forming the backsheet 52, such as described in, by way of non-limiting example, U.S. Published Patent Application. No. 2007/0239130.

Insert Asymmetry

Referring to FIG. 4, the insert 50 may have an insert lateral axis 70 that equally divides its longitudinal length. The insert 50 may have a structure that is asymmetric across the insert lateral axis 70. For purposes of this description, with used with respect to an insert, "asymmetric" and "asymmetry" mean that features, geometry (e.g., shape), materials and/or construction on one side of the insert lateral axis 70 differ substantially in some respect from those on the other side of the insert lateral axis 70. Such asymmetric construction results from having various features of the insert 50 designed to accommodate the body features and functions of the intended wearer (i.e., body contours, excretory and eliminatory functions) as they differ front-to-rear, to enhance containment/absorbency performance, comfort, fit and/or appearance of the wearable absorbent article 10, to economize on use of materials and/or to reduce volume of disposable waste. "Asymmetric" and "asymmetry" do not refer to differences across the insert lateral axis 70 that are attributable to features that may be included on an insert only for purposes of: purely cosmetic coloration or surface decoration; fastening to an outer cover (such as fastener components described herein); user grasping of the insert (such as a grasping structure described herein); as indicia for orienting an insert within an outer cover (such as orientation indicia described herein); or for other purposes substantially unrelated to the body features and functions of the intended wearer as they differ front-to-rear, to affect performance, comfort, fit and/or physical appearance of the wearable absorbent article 10, to economize on use of materials and/or to reduce volume of disposable waste.

As one example, the topsheet 51 may one or more have apertures 63 therethrough, predominately in the crotch and/or the rearward region 55 as suggested in FIG. 4. The apertures 63 may permit liquid or low viscosity fecal material to penetrate the topsheet 51 and reach absorbent materials in the absorbent core 71 more rapidly than would occur without such apertures, enhancing liquid feces absorption and containment capability of the insert 50.

In an embodiment, all or a portion of the rearward region 55 of insert 50 may include acquisition/distribution material 65 but less or no storage material 66 as compared with the forward region 54, as may be seen by comparison of FIGS. 5A and 5B, 5C and 5D, and 5E and 5F, respectively. By this particular absorbent core asymmetry, the storage material 66 may be located predominately in the front of the wearable absorbent article 10 when worn. This may provide a predominate proportion of the insert's urine storage capacity closer to the urine exudation point of the wearer to reduce the likelihood of leakage, and remove potentially uncomfortable and/or unsightly size and bulk from between the wearer's legs or the wearer's backside area, particularly relevant when the storage material 66 becomes swollen with absorbed liquid. Additionally, this particular asymmetry provides for economization of the amount of the storage material 66 used, by locating it in only a portion of the insert 50 rather than substantially along the entire insert 50. The liquid storage capacity of the forward region of the absorbent core 71 may be greater than that of the rearward region of the absorbent core 71 as measured by the Teabag Centrifuge Capacity test disclosed in U.S. Pat. No. 6,278,037.

Figure 5A:
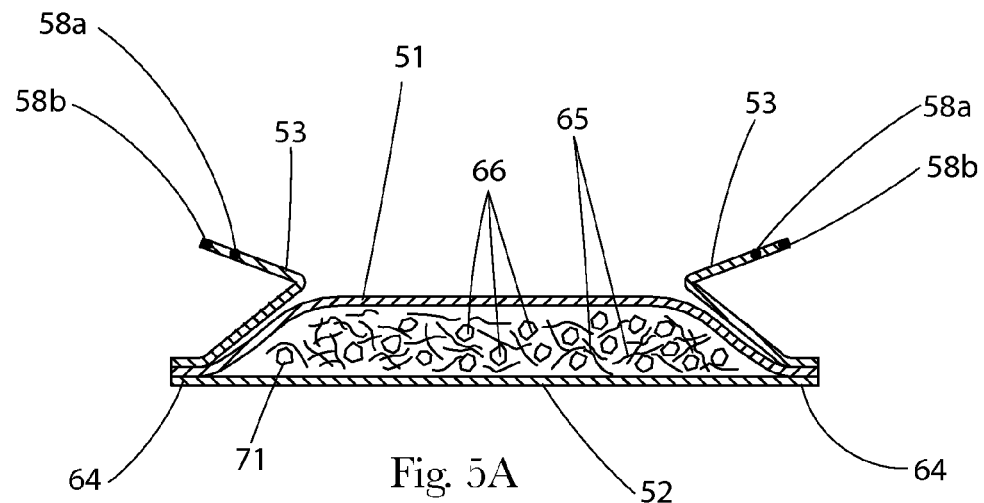
FIG. 5A is a cross-sectional view of an example of an insert such as shown in FIG. 4, taken at line 5A-5A of FIG. 4 in accordance with a non-limiting embodiment of the present disclosure.
Figure 5B:
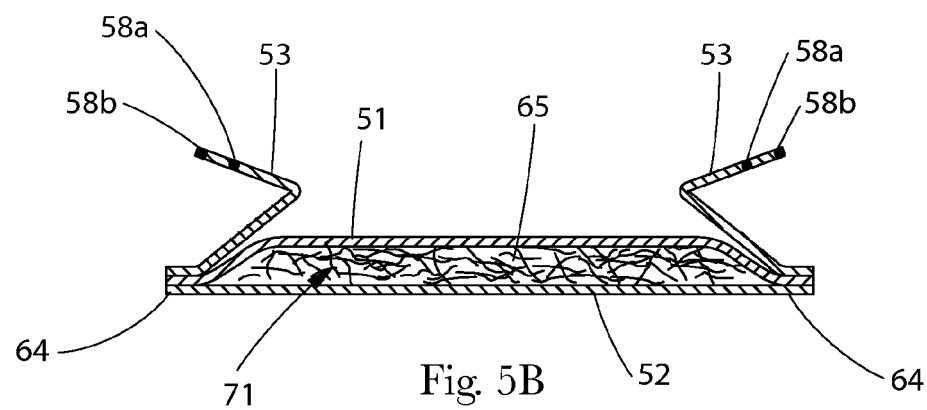
FIG. 5B is a cross-sectional view of an example of an insert such as shown in FIG. 4, taken along line 5B-5B of FIG. 4 in accordance with a non-limiting embodiment of the present disclosure.
Figure 5C:
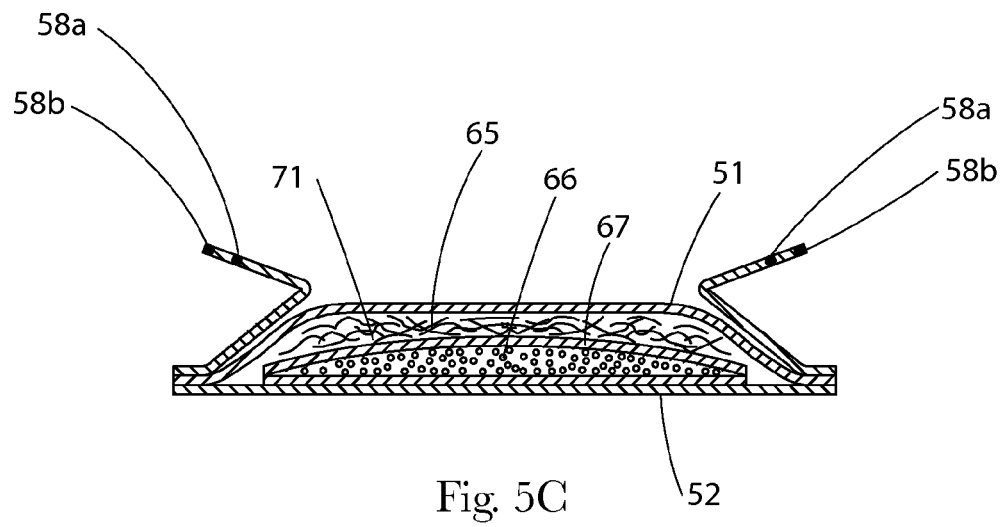
FIG. 5C is a cross-sectional view of another example of an insert such as shown in FIG. 4, taken along line 5C-5C of FIG. 4 in accordance with a non-limiting embodiment of the present disclosure.
Figure 5D:
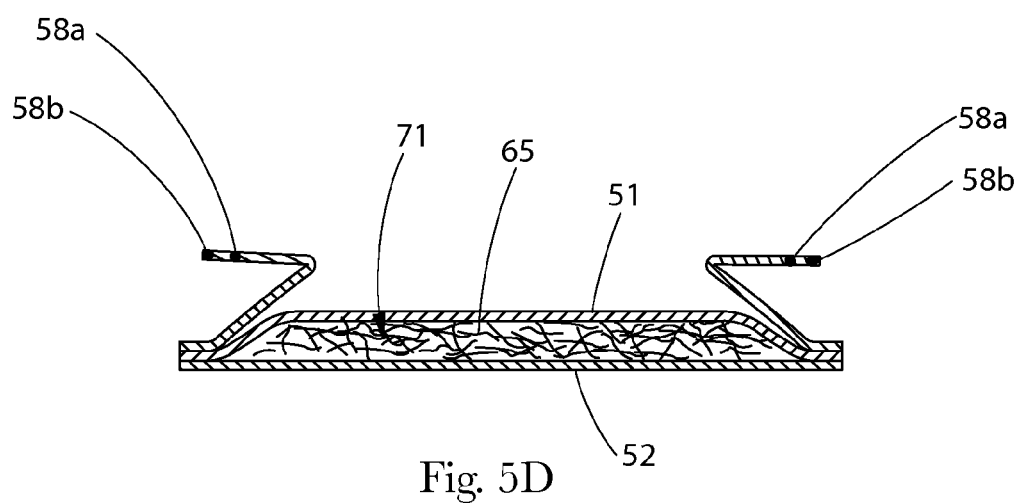
FIG. 5D is a cross-sectional view of another example of an insert such as shown in FIG. 4, taken along line 5D-5D of FIG. 4 in accordance with a non-limiting embodiment of the present disclosure.
Figure 5E:
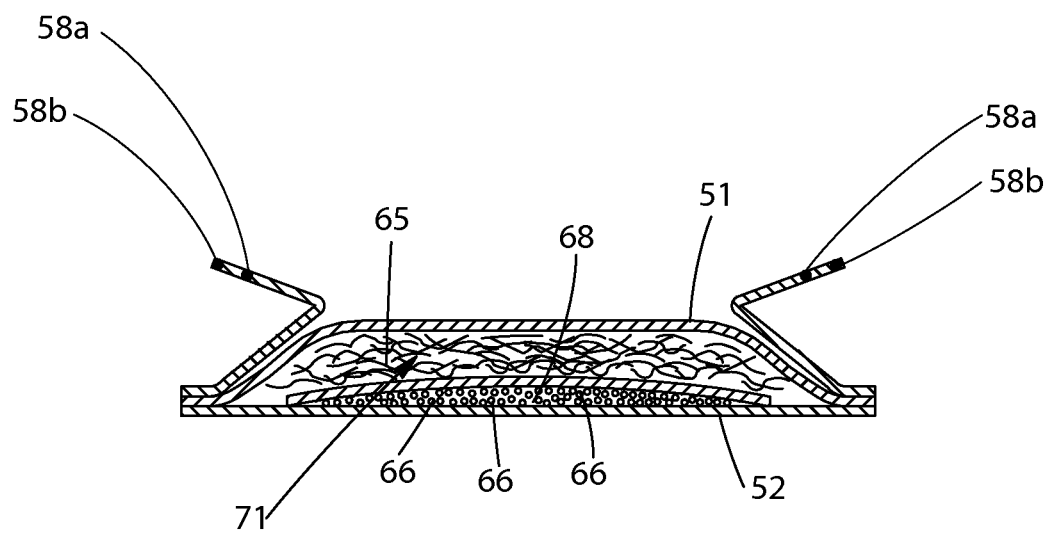
FIG. 5E is a cross-sectional view of another example of an insert such as shown in FIG. 4, taken along line 5E-5E of FIG. 4 in accordance with a non-limiting embodiment of the present disclosure.
Figure 5F:
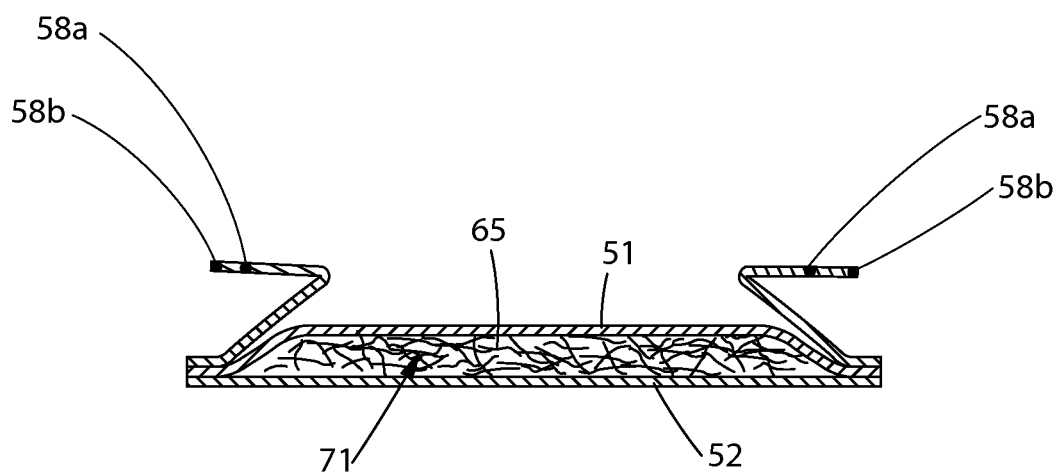
FIG. 5F is a cross-sectional view of another example of an insert such as shown in FIG. 4, taken along line 5F-5F of FIG. 4 in accordance with a non-limiting embodiment of the present disclosure.

Referring to FIGS. 5A, 5C and 5E, in other examples, the absorbent material 66 in the forward region 54 may be, respectively, dispersed within the acquisition/distribution material 65 (FIG. 5A), contained within a separate liquid permeable structure or envelope 67 in fluid communication with the acquisition/distribution material 65 (FIG. 5C); or dispersed on, or within an adherent matrix of, retaining material 68, and in fluid communication with the acquisition/distribution material 65 (FIG. 5E). Conversely, the rearward region 55 may predominately contain the acquisition/distribution material 65, but less storage material 66 as compared with the forward region 54, or none (FIGS. 5B, 5D, 5F). Materials in the forward region 54 also may be disposed according to construction described in one or more of U.S. Patent Application Publication Nos. 2008/0312617, 2008/0312618, 2008/0312628, 2008/0312619, 2008/0312620, 2008/0312621, 2008/0312622, 2008/0312625, 2008/0312624, and U.S. Pat. No. 8,017,827, with a differing construction in the rearward region 55.

In another example, the storage material 66 and the acquisition/distribution material 65 may occupying differing, distinct layers of the absorbent core 71, as suggested by FIG. 5C.

In the event of a pant, the insert may be symmetric across the insert lateral axis 70.

Grasp Structures, Removal and Disposal Aids

Referring to FIGS. 3, and 4, the insert 50 also may include respective user grasp structures 59, 61. The user grasp structures 59, 61 may be provided to enable the user to quickly and easily grasp the insert 50 proximate its respective ends.

Grasp structures as shown and/or suggested may enable the user to more quickly grasp and stretch the insert 50 from a contracted position similar to that depicted in FIG. 3, to an extended position similar to that depicted in FIG. 4, which may be desirable for installing the insert 50 into an outer cover 20.

The user grasp structures 59, 61 may include tab-like extensions as shown in FIGS. 3 and 4, with free ends unattached to the outer cover 20 when the insert 50 is installed therein, which are easily graspable. The user grasp structures 59, 61 may have different forms as well. By way of non-limiting example, user grasp structures may take the form of loop-like extensions extending from the ends of the insert 50, finger holes through the insert 50 proximate the ends thereof, pockets with openings facing the lateral centerline 70 of the insert 50, and other structures that facilitate grasping and pulling of the insert 50 at locations proximate to its ends.

Referring again to FIG. 3, an insert 50 may also include a disposal aid 81, configured to hold the insert 50 in a folded or rolled configuration for convenience of neat handling and disposal following removal of the soiled insert 50 from an outer cover 20. As suggested in FIG. 3, the disposal aid 81 may be in the form of a strip of removable/refastenable tape. Other forms of disposal aids, which serve to hold an insert 50 in a folded or rolled up condition with the topsheet 51 in and the backsheet 52 out, may be used.

Types, Locations and Localization of Fastening Locations

In one example, to enable fastening of respective front and rear fastener components 56, 57 of the insert 50 with respective front and rear attachment zones 33, 32 on the outer cover 20, respective fastening pairs 56, 33 and 57, 32 may include cooperating fastener components. An example of a suitable hook-and-loop fastening system is a VELCRO system, a product of Velcro Industries B.V., components of which are available from Velcro USA, Inc., Manchester, N.H.

However, fastening pairs 56, 33 and 57, 32 need not necessarily include respective components of a hook-and-loop fastening system, and need not necessarily include respective components of a two-component fastening system. Rather, a fastening system may require only one fastener component, or use other types of fastener components. The fastener components used may be adapted to engage, retain, and otherwise hold the insert 50 or a portion thereof. An attachment zone on the outer cover 20 may include a patch of adhesive; a structure having a region of relatively high coefficient of friction; a pocket; flap; strap; or other capturing, holding and/or retaining surface, device or structure. Thus, referring to FIG. 2C in one example, the inside of the outer cover 20 may include one or more pocket structures 32a, 33a situated on or along the inner surface 25 of the outer cover 20, in, e.g., the front waist region 27 or rear waist region 28. Such a pocket structure may have an opening facing downward or upward (relative to the wearer in a standing position, and relative to FIG. 2B). A pocket structure may be adapted to receive, fit and capture, for example, the forward edge and a portion of the forward region 54 of the insert 50. A pocket structure 32a, 33a may have an opening facing the lateral axis 45, such that an end of the insert 50 may be inserted therein and retained thereby. A pocket structure may alternatively have an opening facing away from the lateral axis 45, such that an end of the insert 50 may be inserted therein and retained thereby, and then the insert 50 may be folded back over such opening and toward the lateral axis 45.

Insert End Support Stiffeners

In an embodiment, referring to FIGS. 3 and 4, an end support stiffener 60 and/or 62 may be included at one or both ends of the insert 50. Such an end support stiffener may serve to aid the user in engaging the insert 50 with the outer cover 20, and to help the insert 50 maintain its intended shape and configuration while being worn beneath an outer cover, i.e., help maintain its intended shape, position and gasketing functions (e.g., of the standing cuffs 53). An end support stiffener 60, 62 also may help control the corners of the insert 50 regardless of the size, type or location of fastener components included on the insert 50. In addition to providing resistance to longitudinal pull of the cuff edges 58, the end support stiffeners 60, 62 may provide resistance to bending in any direction or plane. An end support stiffener 60, 62 may be affixed to, or incorporated within, the insert 50 proximate one or both ends thereof as suggested by FIGS. 3 and 4.

Referring to FIG. 4, one or more of the end support stiffeners 60, 62 may be disposed in a lateral orientation with respect to the insert 50 and formed of any flat, sheet-like or card-like material, or any flat, stiffened assembly that adds stiffness to the insert end that exceeds the stiffness of the adjacent portion lying nearer the insert lateral axis 70.

In various embodiments, a pull-on wearable absorbent article or pull-on pant comprises a reusable outer cover 20 and a disposable absorbent insert 50, as discussed above. The pull-on wearable absorbent article may comprise at least one grasping aid on, joined to, formed with, formed in, or formed from a portion of the reusable outer cover 20, for assisting in the application of the wearable absorbent article onto a wearer or for assisting in removal of the wearable absorbent article from the wearer. The grasping aids of the present disclosure are designed to withstand the forces necessary to apply and/or remove the pull-on wearable absorbent article including insertion of the wearer's feet through the leg openings, elevating the pull-on wearable absorbent article up the wearer's legs and over the wearer's buttocks, achieving an ideal snug fit, and lowering the pull-on wearable absorbent article.

The grasping aid embodiments, described in further detail herein, are generally not limited in location or number. Some embodiments show the grasping aids presented as a pair, however, the present disclosure specifically includes grasping aids appearing singularly and in numbers greater than two, such as three or four, for example. Furthermore, in the embodiments comprising more than one grasping aid, the grasping aids may be placed symmetrically or non-symmetrically about the reusable outer cover and/or about the reusable outer cover's lateral axis and/or longitudinal axis. It should be further emphasized that locations of the grasping aids in the embodiments listed below are not to be limiting and are merely example embodiments. Grasping aid placement may occur at any suitable location on the reusable outer cover such that the grasping aid may be grasped by the wearer or caregiver.

In FIGS. 6A-14, only reusable outer covers are illustrated, however, it will be appreciated that these outer covers are configured to be joined to disposable absorbent inserts to form pull-on wearable absorbent articles or pull-on pants. In some figures, the insert fastening components of the reusable outer covers are not illustrated, but it will be understood that such insert fastening components may be present at any suitable locations, as described above.

In an embodiment, a reusable outer cover may have a first grasping aid and a second grasping aid. The first grasping aid may be positioned on a first side of the longitudinal axis 46 of the reusable outer cover 20 and the second grasping aid may be positioned on a second side of the longitudinal axis 46. In an embodiment, the first grasping aid may be positioned on a first side of the lateral axis 45 of the reusable outer cover 20 and the second grasping aid may be positioned on a second side of the lateral axis 45. In other embodiments, any number of grasping aids may be positioned on one side or the other of the lateral and/or longitudinal axes 45 and 46, respectively.

In an embodiment, FIG. 6A illustrates a perspective view of an example grasping aid configured as a flap 200 extending from a portion of the reusable outer cover 20 near the front and back waist edges 21 and 22 (hereafter together referred to as 21). The flap 200 is, generally, a stratum disposed adjacent to a portion of a garment-facing surface, or outer surface, of the reusable outer cover 20 proximate (e.g., within 1 mm to 30 mm) to the waist edge 21 such that, during application and/or removal of the reusable outer cover 20, the fingers of the wearer or caregiver may be inserted under, into, or through a gap 210 or one or more pockets formed between the garment-facing surface of the reusable outer cover 20 and the stratum. In an embodiment, the flap 200 may be intermittently joined to the garment-facing surface of the reusable outer cover 20 about the length of the flap 200, or a portion thereof, to produce one or more finger sized pockets between the garment-facing surface of the reusable outer cover 20 and the stratum. This feature may provide stability to the flap. While not limited in theory, the flap 200 may allow the individual applying and/or removing the reusable outer cover 20 to cup the flap between the fingers and palm or encircle the flap 200 by fingers and a thumb. In an embodiment, the flap 200 may have a first end 209, a second end 211, and a central portion 213. The flap 200 may be attached to a portion of the reusable outer cover 20 at the first end 209, at the second end 211, and/or in the central portion 213. The central portion 213 of the flap 200 may form a pocket (i.e., gap 210) configured to receive one or more fingers if points of attachment to the reusable outer cover 20 are present within the central portion 213.

In various embodiments, the flap 200 may be located longitudinally at or proximate to the waist edge 21 and laterally span over a seam or side seam. The flap 200 may also be located at other locations, such as in the front waist region 27 and/or the rear waist region 28 of the reusable outer cover 20. In other embodiments, when two flaps 200 are present, one flap 200 may extend over or span a first seam between the front and rear waist regions 27 and 28 and other flap 200 may extend over or span a second seam between the front and rear waist regions 27 and 28. In other embodiments, a first flap 200 may be positioned in the front waist region 27 and a second flap 200 may be positioned in the rear waist region 28. The flap 200 may extend from the waist edges 21 or may extend from another portion of the reusable outer cover 20. In certain embodiments, the flap 200 may be joined to the reusable outer cover 20 or may be formed with or from a portion of the reusable outer cover 20. The flap 200 may either be of unitary or multiple construction as represented in the cross-sectional views (taken along sectional line 6-6 of FIG. 6A) of the flap in FIG. 6B and FIG. 6C, respectively.

The unitary construction of FIG. 6B entails a stratum 250 of the material, either a lamina or laminate, of the reusable outer cover 20 extending beyond the waist edge 21 and folded radially away from the garment-facing surface of the reusable outer cover 20. A portion of the stratum 250 is joined to the reusable outer cover 20. The resulting flap 200 forms a gap 210 of an effective length such that a wearer or caregiver may, easily engage the flap 200 with his or her fingers. The effective length is the length of the flap 200 measured on the garment-facing surface from the waist edge 21 longitudinally inward to the lower end 220 of the flap 200. The effective length may be from about 10 mm to about 50 mm or from about 20 mm to about 30 mm, specifically reciting all 1 mm increments within the specified ranges and all ranges formed therein or thereby. A portion of the flap 200 may be joined to the garment-facing surface of the reusable outer cover 20 in order to keep the flap 200 snug against the garment-facing surface of the reusable outer cover 20 when the flap 200 is not engaged by the wearer or the caregiver. Furthermore, the joining prevents, or at least inhibits, the flap 200 from unfolding; thus, preserving the integrity of the flap 200. The flap 200 may have a joining point 205, which runs substantially laterally along, or otherwise along, a portion of the reusable outer cover 20 and is generally in proximity to the waist edge 21, and/or joining points 260, which run substantially longitudinally along, or otherwise along, portions of the reusable outer cover 20 and may generally be in proximity to the distal longitudinal edges of the flap 200. The joining points may be continuous or discontinuous. If a lateral, or substantially lateral (+/−25 degrees from the lateral axis), joining point is absent, the flap 200 may be cut along the waist edge 21 and through to a hingepoint 240. The cut may extend over the complete width of the flap 200 or a portion of the width of the flap 200. The cut should have sufficient width to allow penetration of the wearer's or caregiver's fingers so that the flap 200 may be at least partially encircled by the wearer's hand or the caregiver's hand. The cut may further extend over a portion of the flap 200 to yield a shaped grasping aid.

The multiple construction of FIG. 6C entails a discrete stratum 250 that is joined to the garment-facing surface of the reusable outer cover 20 at a connection point 230. The connection point 230 is the location on the reusable outer cover 20 where the flap 200 is joined. The connection point 230, as shown in FIG. 6C, may be located adjacent to the waist edge 21. The connection point 230 may exist anywhere on the reusable outer cover 20 limited only such that the flap 20 may be engaged by the wearer or caregiver. The connection point 230 may also be on the wearer-facing surface of the reusable outer cover 20 with the resulting flap 200 extending over the waist edge 21 and away from the garment-facing surface of the reusable outer cover 22. The flap 200 should form a gap 210 of an effective length, as described above, such that a wearer or caregiver can easily engage the flap 200 with his or her fingers. The effective length may be from about 10 mm to about 50 mm or from about 20 mm to about 30 mm, specifically reciting all 1 mm increments within the specified ranges and all ranges formed therein or thereby. The flap 200 may be joined to the reusable outer cover 20 in order to keep the flap 200 snug against the garment-facing surface of the reusable outer cover 20 when the flap 200 is not engaged by the wearer or caregiver and to prevent, or at least inhibit, the flap 200 from unfolding during use. The flap 200 may have a joining point 205, which runs substantially laterally (+/−25 degrees from the lateral axis) along a portion of the reusable outer cover 20 and is generally in proximity to the waist edge 21, and/or joining points 260, which run substantially longitudinally (+/−25 degrees from the longitudinal axis) along a portion of the reusable outer cover 20 and are generally in proximity to the distal longitudinal edges of the flap 200. The joining points may continuous or discontinuous. If no joining point 205 exists, the flap 200 may be constructed so that the flap 200 may be at least partially encircled by the wearer's or caregiver's hand or one or more fingers. If no joining point 205 exists, the flap 200 may be of a substantially hyperbolic shape as shown as an example in FIG. 6D. In FIG. 6D, the grasping aid 200 may comprise a first end 201 and a second end 203. The reusable outer cover 20 may comprise a portion. The grasping aid 200 may be joined to the portion at the first end 201 and at the second end 203. A central portion 207 (i.e., portion between the first end 201 and the second end 203) of the grasping aid 200 may be free from attachment to the portion of the reusable outer cover 20 and form a loop between the first end 201 and the second end 203.

The flap 200 may be "joined" to the reusable outer cover by an adhesive, heat bonds, pressure bonds, ultrasonic bonds, sewing, stitching, dynamic mechanical bonds, or combinations thereof. The term "joined," as used herein, can include any of the above-listed attachment techniques.

The flap 200 may be located at any suitable place and in any suitable configuration and/or orientation on the reusable outer cover 20 so that the flap 20 may be engaged by the wearer or caregiver. The dimensions and shape of the flap 200 are limited only such that the reusable outer cover maintains a comfortable fit and the flap 200 does not interfere, or substantially interfere, with the application of other outer garments (i.e., shorts or a gown) being positioned over the reusable outer cover 20. The flap 200 is not limited in width and may span any portion of the reusable outer cover up to circumscribing the entire reusable outer cover 20. The flap 200 may be continuous or discontinuous about the reusable outer cover. The flap 200 may be constructed of any suitable material, such as wovens, knitted materials, plastics, nonwovens, foams, and/or polymeric materials.

The flap may comprise a laminate that exhibits a stretchability from about 5% to about 200% or from about 50% to about 100%, specifically reciting all 1% increments within the specified ranges and all ranges formed therein or thereby, when subjected to pull forces of up to 2 kgf. In another embodiment, the flap may be non-stretchable and may have a relaxed length greater than the distance the flap extends between attachment points to the reusable outer cover 20. In such an embodiment, a portion of the reusable outer cover 20 may stretch when a force is applied to the flap instead of the flap stretching. In other embodiments, the flap and a portion of the reusable outer cover where the flap is attached thereto may both be able to, or not be able to, stretch. The flaps may be three dimensional and may comprise dart, folds, textures, or the like.

In an embodiment, the flap may be about 10 mm to about 50 mm, about 20 to about 40 mm, or 30 mm in length, specifically reciting all 1 mm increments within the specified ranges and all ranges formed therein or thereby. The width and/or length of the flap may be dependent upon the size of the reusable outer cover to which the flap is affixed. In an embodiment, the width of the flap may be great enough to span from a portion of the front waist region 27 to a portion of the rear waist region 28.

In an embodiment, FIG. 7A illustrates a perspective view of an embodiment of a grasping aid configured as a tab 300 extending from a portion of the reusable outer cover 20. The tab 300 may be generally a stratum disposed adjacent to a garment-facing surface of the reusable outer cover 20 such that, during application and/or removal of the reusable outer cover 20 from the wearer, the tab 300 may be engaged by pinching the tab 300 between the fingers of the wearer or caregiver. In an embodiment, the tab 300 may be a unitary tongue of material comprising a portion of the reusable outer cover 20. In other embodiments, the tab 300 may be a separate material than the reusable outer cover 20, wherein the separate material is attached to the reusable outer cover 20. The tab 300 may extend in a direction such that the one dimension of the tab 300 parallels, or substantially parallels, the waist edge 21. The location and dimensions of the tab 300 are limited only by the wearer's ability to reach and engage the tab 300. In other configurations, one or more tabs may be positioned in the front waist region 27 and one or more tabs may be positioned in the rear waist region 28. The one or more tabs 300 may be combined with other grasping aids, such as texture zones, loops, or other suitable grasping aids.

While FIG. 7A illustrates an example location of the tabs 300 as extending from the waist edge 21, the tabs 300 may also be located anywhere on the reusable outer cover 20 such that the wearer or caregiver can engage the tabs 300 while applying the reusable outer cover 20. The tabs 300 may be positioned along the side portions of the reusable outer cover 20. Furthermore, the tabs 300 may be joined to the garment-facing surface, the wearer facing-surface, and/or extend intermediate these surfaces of the reusable outer cover 20.

The dimensions of the one or more tabs 300 may be of an effective size such that a wearer or caregiver can engage the tab 300 with his or her fingers. The maximum dimensions of the tab 300 are limited only such that the reusable outer cover 20 maintains a comfortable fit and the tab 300 does not interfere, or substantially interfere, with application of other outer garments (i.e., shorts, gown) over the reusable outer cover 20. The tab may have a longitudinal length of about 10 mm to about 50 mm or about 20 mm to about 30 mm, specifically reciting all 1 mm increments within the specified ranges and all ranges formed therein or therein. While not limited to any particular shape, the illustrated example tabs 300 have a substantially parabolic shape.

In an embodiment, referring to FIG. 7B, the waist edge 21 may be substantially sinusoidal. The reusable outer cover 20 generally may comprise multiple tabs, such as two tabs being positioned in the rear waist region 28 and one tab being positioned in the front waist region 27.

The one or more tabs 300 may be discrete pieces of material affixed to the reusable outer cover 20. If the tabs 300 are discrete pieces of material rather than a unitary tongue of a portion of the reusable outer cover 20, the tabs 300 may be secured to the reusable outer cover 20 by any joining technique known to those of skill in the art, such as through the use of adhesives, heat bonds, stitches, pressure bonds, ultrasonic bonds, dynamic mechanical bonds, or combinations thereof. The tabs 300 may be affixed proximate to the waist edge 21, but the location of the tabs 300 is not so limited. The tabs 300 may be constructed from any suitable materials, such as wovens, knitted materials, nonwovens, foams, and polymeric materials.

FIG. 8A illustrates a perspective view of an embodiment of a grasping aid configured as a ridge 400 protruding from a portion of the reusable outer cover 20. The ridge 400 may be a protrusion extending from at least the garment-facing surface of the reusable outer cover 20 such that the ridge 400 provides increased caliper which may be engaged by the wearer's or caregiver's fingers. In an embodiment, the ridge 400 may be positioned proximate to (e.g., within 1 mm to 30 mm) the waist edge 21. The ridge 400 may be stretchable or compressible. The ridge 400 may have a minimum effective cross-dimension such that the ridge 400 is a grippable protuberance for the wearer or caregiver. The maximum effective cross-dimension of the ridge 400 may only be limited such that the reusable outer cover maintains a comfortable fit and the ridge 400 does not interfere, or substantially interfere, with the application of other outer garments (i.e., prohibit self-application of shorts, gown, etc.). The ridge 400 may have an effective cross-dimension of about 2 mm to about 15 mm or of about 5 mm to about 8 mm, specifically reciting all 1 mm increments within the specified ranges and all ranges formed therein or thereby. The effective cross-dimension is the difference between the maximum caliper of the reusable outer cover 20 at the ridge 400 subtracted by the minimum caliper of the reusable outer cover 20 as measured immediately below (i.e., "below" being the downward direction of a reusable outer cover 20 when worn) the ridge 400. Caliper, as used herein, generally refers to a linear dimension as measured orthogonal to the plane defined by the longitudinal and lateral axes 46 and 45. The ridge 400 may be stretchable or compressible.

In an embodiment, the ridge 400 may comprise a spacer 410 interposed between at least one layer of the reusable outer cover. The spacer 410 may be comprised of any suitable materials, such as wovens, nonwovens, plastics, foams, and polymeric materials. The spacer 410 may be configured to have any suitable shape and size that creates a graspable protuberance while still maintaining a comfortable and non-irritating fit to the wearer. In an embodiment, referring to the cross-sectional view of FIG. 8B, taken along the sectional line 8-8 of FIG. 8A, the spacer 410 may comprise an open-cell foam material with a relatively semi-circular cross-sectional dimension with the rounded edge being garment-facing. The spacer 410 may also have any other suitable cross-sectional shape. The spacer 410 is illustrated, as an example, interposed between two layers, an inner layer 420 and outer layer 430. A layer can be any single lamina or combination of laminae (i.e., a laminate) typically used in the construction of the reusable outer cover 20. The spacer may span all of, or a portion of, the front and rear waist regions 27 and 28 of the reusable outer cover 20 and may be interposed between the outer layer 430 and the inner layer 420. The layers may be joined, sewn, bonded, or glued together at the contact points 440 immediately adjacent to or proximate to the spacer 410. Optionally, the spacer 410 itself may be welded to, sewn to, bonded to, adhesively attached to, or joined to, one or more layers. This process secures the spacer 410 in place and prevents it, or at least inhibits it, from shifting within the interstice of the layers. In an embodiment (not illustrated), the spacer may be interposed between the inner layer or outer layer of the reusable outer cover and a discrete patch comprised of a lamina or laminate. The patch may be welded to, sewn to, bonded to, adhesively attached to, or joined to the layer at the contact points immediately adjacent to, or adjacent to, the spacer. The spacer 410 may also be welded to, sewn to, bonded to, adhesively attached to, or joined to the garment-facing surface of the reusable outer cover 20.

Furthermore, in an embodiment illustrated as a cross-sectional view in FIG. 8C (taken along the sectional line 8-8 of FIG. 8A), the spacer 410 may be interposed between a single layer 425, either a lamina or laminate, that is folded around the spacer 410. In such a configuration, the single lamina or the laminate is welded to, sewn to, bonded to, adhesively attached to, or joined to itself at contact points 440 immediately adjacent to, or generally adjacent to, the spacer 410; thus, sealing the spacer 410 in place. It should be noted that, in some embodiments, a single contact point may exist especially if the spacer 410 is disposed immediately adjacent to the waist edge 21.

In an embodiment, FIG. 8D illustrates an example cross-sectional view of the ridge 400 as a cap 460 along a portion of, or all of, the waist edge 21 of the reusable outer cover 20. The cap 460 may comprise a foam material but a variety of wovens, nonwovens, plastics, and polymerics may also be utilized. The cap 460 may be affixed along the waist edge 21, the garment-facing surface adjacent the waist edge 21, and/or the wearer-facing surface adjacent the waist edge 21. Another embodiment involves the ridge 400 being formed by folding or rolling a portion of the reusable outer cover 20 about the waist edge 21 to provide a palpably raised surface. The interface between the reusable outer cover and the resulting fold or roll may be joined to prevent, or at least inhibit, the fold or roll from unraveling during use.

The affixation and joining of any of the ridge 400 embodiments may be performed by any joining technique known to those of skill in the art, such as through the use of adhesives, heat bonds, pressure bonds, sewing, ultrasonic bonds, dynamic mechanical bonds, or combinations thereof. Furthermore, the ridge 400 may fully, partially, or intermittently circumscribe the reusable outer cover or portions thereof. While partially circumferential peripheral ridges are illustrated, the ridge 400 will serve the same functional purpose even where fully or intermittently circumscribing the reusable outer cover 20.

In an embodiment, FIG. 9A is a perspective view of a grasping aid configured as a texture zone 500 within, on, formed in, formed on, or joined to the reusable outer cover 20 with a distinct grippable surface characteristic. Any suitable number of texture zones 500 may be provided and these textures zones may have any suitable size and shape. A texture zone 500 with a distinct grippable surface characteristic refers to a palpable difference in texture, pliancy, tackiness, three-dimensionality, and/or friction of the texture zone compared to a surface of the reusable outer cover outside of the texture zone. The distinct grippable surface characteristic may be an increase in friction. The distinct grippable surface characteristic may be imparted to the texture zone 500 by a variety of methods. The outer-most surface or garment-facing surface of the reusable outer cover outside of the texture zone 500 may have a coefficient of static friction from about 0.15 to about 0.25. Coefficient of static friction values at these relatively low levels facilitates application of outer garments over the reusable outer cover 20. The texture zone 500 may have a distinct grippable surface exhibiting a coefficient of static friction from greater than about 0.3 to less than about 4.0, from about 0.4 to about 2.0 or greater, or from about 0.7 to about 1.5. The coefficient of static friction is measured according to the test method disclosed in U.S. Pat. No. 6,626,879, entitled "Disposable Absorbent Article Having Article Retention Zones" issued to Ashton et al. on Sep. 20, 2003.

In an embodiment, the characteristic can be imparted to the texture zone by lamination with one or more laminae that exhibit a distinct grippable surface characteristic. The texture zone may be laminated by coating or patches. When the texture zone is laminated by coating, a suitable coating composition may be used to increase the coefficient of friction including, but not limited to, coatings of pressure-sensitive materials or of tacky materials. Suitable coatings include ethylene vinyl acetate copolymers, polyvinyl acetate, styrene-butadiene, cellulose acetate butyrate, ethyl cellulose, acrylics, synthetic rubber hot melt, and other hot melts. Methods for coating include, but are not limited to, extrusion, coating, slot coating, gravure printing, and screen printing. When the texture zone is laminated by patches, the patches can be made from a number of different materials that are thin, flexible, and that can be affixed to the texture zone. Examples of materials from which such patches can be made are polymeric films, apertured films, fibrous nonwoven sheets, scrims, scrim nettings, or fibrous flocked substrates. The patches may be affixed to or joined to the texture zone by affixation means known to those of skill in the art with preference toward heat/pressure affixation. A more detailed discussion of lamination by coating or patches is contained in above-referred to U.S. Pat. No. 6,626,879, particularly the disclosure on retention zones.

In an embodiment, the characteristic may be imparted to the texture zone by constructing the texture zone from a material that inherently exhibits the characteristic. An open cell foam may be used to provide a texture zone with the abovementioned coefficients of static friction; however, a variety of nonwoven, woven, polymeric, rubber, and foam materials exist exhibiting a sufficient coefficient of static friction so as to assist the grasping of the reusable outer cover. Additionally, the characteristic can be imparted to the texture zone by mechanical or chemical processing or any other suitable methods known to those of skill in the art.

In an embodiment, the texture zone 500 may comprise one or more ridges, bumps, or raised portions (see e.g., FIG. 9B). These ridges, bumps, or raised portions may have any suitable arrangement or configuration or number in a specific texture zone. If two or more texture zones are provided on a reusable outer cover, they may have the same or different configurations, textures, and/or orientations. The ridges bumps, or raised portions may be uniform or non-uniform throughout a texture zone.

Additional surface characteristics of the texture zone instead of, or in addition to, an increased static friction coefficient are also within the scope of the present disclosure. The texture zone may exhibit a texture such that the material comprising the texture zone has a palpable quality. The texture zone may exhibit a pliancy such that the material comprising the texture zone yields to touch. The texture zone may exhibit a tackiness such that the material comprising the texture zone has a slightly adhesive or gummy feel to the touch.

Alternately, the one or more texture zones may be located anywhere on the reusable outer cover and are not limited to the illustrated locations. The texture zone(s) need only be located such that they may be grasped by the wearer or caregiver. Furthermore, the texture zones are not limited in dimension and may span any portion of the reusable outer cover up to circumscribing and covering the entire garment-facing surface of the reusable outer cover. The texture zones may also be intermittent around a perimeter of the reusable outer cover. The texture zones may circumscribe the reusable outer cover 20, partially circumscribe the reusable outer cover 20 as seen in FIG. 9A, and or comprise numerous discrete areas as seen in FIG. 9B which may be of varying size, shape, and dimension. The texture zones may be combined with any of the other grasping aid embodiments disclosed herein to enhance the ability of a wearer or a caregiver to don the pull-on pant.

In an embodiment, FIG. 10 is a perspective view of grasping aids configured as loops 600. FIG. 10 illustrates an embodiment having dual loops extending from approximately the midpoint of the sidewalls of the reusable outer cover 20. Any suitable number of loops may be provided at any suitable location. The loops 600 may be sized and/or configured to receive one or more fingers or a thumb. In an embodiment, the loops 600 may be formed from a unitary tongue of material comprising a portion of the reusable outer cover 20 extending beyond the waist edge 21. The tongue may be folded back onto itself, and the distal edge of the tongue may be affixed to itself or to the garment-facing surface or wearer-facing surface of any lamina within the reusable outer cover 20 and in proximity to the waist edge 21. The resulting appendage is a loop 600 that may be grasped while applying or removing the reusable outer cover 20. In an alternate embodiment, the loop 600 may be formed from a discrete piece of woven, rubber, nonwoven, foam, or polymeric film material. The distal ends of the piece may be welded, sewn, bonded, adhesively attached, or joined to form the loop. The connected ends of the loop may be affixed to the reusable outer cover 20, such as by being interposed between two layers of the reusable outer cover proximate to the waist edge 21. Alternately, the attachment of the distal ends of the strip and the affixation of the strip to the reusable outer cover 20 may be performed in a single step by any welding, sewing, bonding, adhesively attaching, or joining mechanisms known to those of skill in the art. Additionally, the discrete loops may be affixed to the garment-facing surface of the reusable outer cover 20 at any place such that the loop may be engaged by the wearer or caregiver and is not limited to that shown proximate to the waist edge 21.

In an embodiment, a loop may extend from the waist edge 21 and within the front and/or rear waist regions of the reusable outer cover 20. Placement of such a loop may assist the wearer or caregiver in executing the finish.

In an embodiment, the loop 600 may be a stratum of material at least partially welded, sewn, bonded, adhesively attached, or joined to the garment-facing surface of the reusable outer cover 20. The stratum may be welded, sewn, bonded, adhesively attached, or joined at opposing ends with a free portion therebetween, such that a loop may be formed between the stratum and the reusable outer cover. The resulting loop may resemble a "belt loop" as found on traditional garments such as dress pants or jeans.

Alternatively, the loop may comprise one or more strings, ropes, threads, yarns, twines, or other suitable material or materials. In an embodiment, the loop may be comprised of a natural or synthetic fiber. At one or more points along the circumference of the waist edge 21, the loop may protrude from the waist edge 21 or not protrude upwardly from the waist edge 21, but instead protrude laterally (when the reusable outer cover is on the wearer).

Figure 11A:
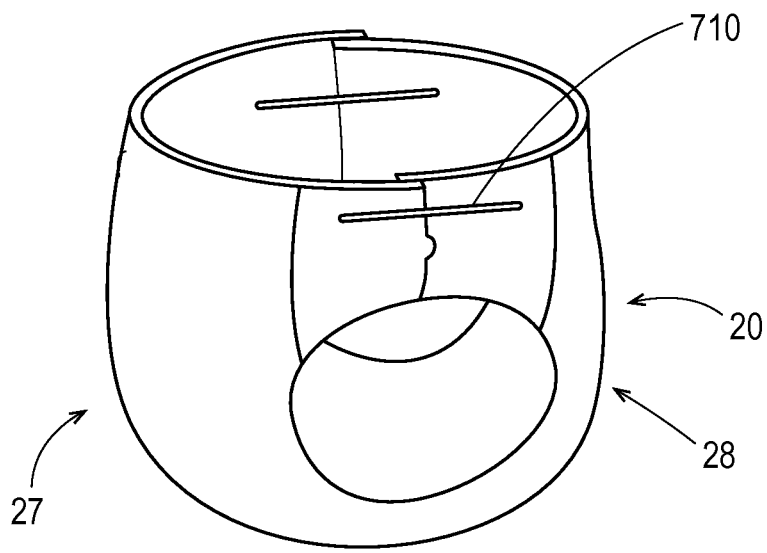
FIG. 11A is a perspective view of a reusable outer cover for a pull-on wearable pant comprising a grasping aid configured as an aperture comprising a slit formed in the reusable outer cover in accordance with a non-limiting embodiment of the present disclosure.

In an embodiment, FIG. 11A is a perspective view of a grasping aid configured as an aperture or opening within the reusable outer cover 20. Any suitable number of apertures may be provided in the reusable outer cover 20. In an embodiment, the aperture may be positioned proximate to the waist edge 21 or at any other suitable location on the reusable outer cover 20. The aperture may be a slit 710 through a portion of the reusable outer cover 20 such that a wearer or caregiver can insert his or her fingers through the slit 710 and grasp a portion of the reusable outer cover 20 proximate to the slit 710. The slit 710 may be linear and substantially parallel to the waist edge 21 or otherwise positioned and/or configured. The slit 710 may be non-linear and may comprise one or more arcuate portions. Any suitable number of slits 710 having any suitable orientation or configuration may be provided on the reusable outer cover 20 at any suitable locations. The slits 710 may be reinforced to provide increased strength and resistance to tearing or increased usability (e.g., deforms less when pulled). The reinforcing material may be any suitable material, such as a woven material or an elastic material, for example.

Figure 11B:
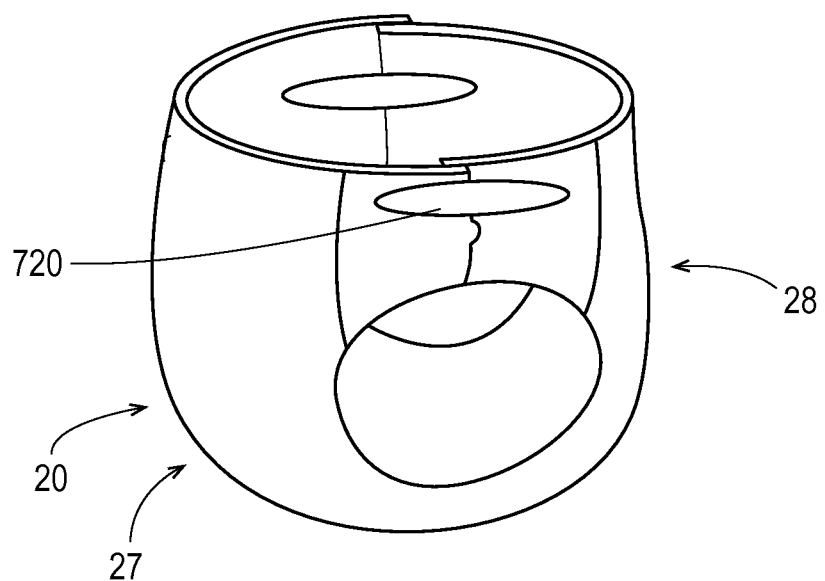
FIG. 11B is a perspective view of a reusable outer cover for a pull-on wearable pant comprising a grasping aid configured as an aperture comprising a distinct hole in accordance with a non-limiting embodiment of the present disclosure.

In an embodiment, the aperture may comprise one or more distinct holes 720 through the reusable outer cover 20 as illustrated in FIG. 11B. A distinct hole 720 is an aperture where the void created has a non-negligible area (e.g., greater than 1 sq. in). Such a distinct hole 720 would operate in a manner similar to the slit 710, while being more conspicuous to the wearer or caregiver. The distinct hole 720 may be elliptical, round, triangular, or any other suitable shape. Any suitable number of distinct holes 710 having any suitable configuration or orientation may be provided on the reusable outer cover 20 at any suitable locations. The distinct hole 710 may be reinforced to provide increased strength and resistance to tearing or increased usability (e.g., deforms less when pulled). The reinforcing material may be any suitable material, such as a woven material or an elastic material, for example.

The dimensions of the one or more apertures may be of an effective size such that a wearer or caregiver can engage an aperture with his or her fingers. The dimensions of the apertures are limited only such that the reusable outer cover maintains a comfortable fit and functionality when worn by a wearer. While the one or more apertures may be ideally located on or along the side portions of the reusable outer cover and somewhat proximate to the waist edge 21, one of skilled in the art will recognize that the apertures may be located at any suitable location in the reusable outer cover so long as the aperture may be engaged by the wearer or caregiver and so that the aperture does not cause bodily exudate leakage from the reusable outer cover. Furthermore, the aperture may span a side seam in the reusable outer cover or may be located solely in the front waist region 27 and/or the rear waist region 28.

Further embodiments may result from the combination of any of the aforementioned grasping aids. For example, a reusable outer cover may comprise a grasping aid configured as a tab, with the tab itself further comprising a grippable region. Use of one or more different grasping aid embodiments within a single reusable outer cover is within the scope of the present disclosure. For example, a reusable outer cover may comprise a grippable region and a loop.

In an embodiment, a reusable outer cover comprising one or more of the grasping aid embodiments of the present disclosure may be packaged in a kit comprising one or more of the reusable outer covers and/or one or more disposable absorbent inserts. The reusable outer covers may be positioned within a kit such that the grasping aids are readily accessible. Readily accessible means that the grasping aids are visible to the wearer or caregiver and that the grasping aids may be grasped and used for removal of the reusable outer cover from the kit. The disposable absorbent inserts may also comprise grasping aids and may be positioned within the kit in the same or a similar fashion. The kit may require activation so that the reusable outer covers become accessible (e.g., opening of a lid, removal of a panel, etc.). In an embodiment, the kit may be defined by numerous reusable outer covers bound together as an entity and covered by a thermoplastic film overwrap. One kit is represented in U.S. Pat. No. 5,934,470, issued to Bauer et al., on Aug. 10, 1999. This kit enables reusable outer cover to be delivered to and purchased by a consumer while economizing space. The thermoplastic film cover may comprise an opening mechanism to allow removal of a portion of the thermoplastic film cover and access to the reusable outer covers. A typical opening mechanism may include a substantially continuous line of weakness, such as perforations within the thermoplastic film cover. An example opening mechanism is presented in U.S. Pat. No. 5,036,978, issued to Frank et al., on Aug. 6, 1991.

Upon activation of the opening mechanism, the reusable outer cover may be presented individually or multiply for removal from the kit. Regardless of such presentation, the grasping aid may be visible and graspable. The grasping aid may be presented by the manner in which the kit is opened. The grasping aid may be presented in a manner in which the reusable outer cover is folded and/or stacked within the kit. The grasping aid may be presented by the mere size, shape, and/or position of the grasping aid.

In an embodiment, the grasping aids of the present disclosure may extend from a portion of the front waist region 27 to a portion of the rear waist region 28 and may span a seam between the front waist region and the rear waist region (see e.g., FIG. 6A). The grasping aids may form pockets (e.g., FIG. 6B) or loops (e.g., FIG. 10). These loops or pockets may be configured to receive one or more fingers or a portion of a hand.

The grasping aids of the present disclosure may be differentiated visually from other portions of the reusable outer covers. In an embodiment, the visual differentiation may be visual (e.g., color) and/or tactile (e.g., texture).

In an embodiment, the grasping aids of the present disclosure may be comprised of materials having an elastic modulus that is different than, the same as, greater than, or less than the elastic modulus of the reusable outer cover. In other instances, portions of the reusable outer cover comprising or forming the grasping aids may have an elastic modulus that is different than, the same as, greater than, or less than the elastic modulus of other portions of the reusable outer cover.

Figure 12:
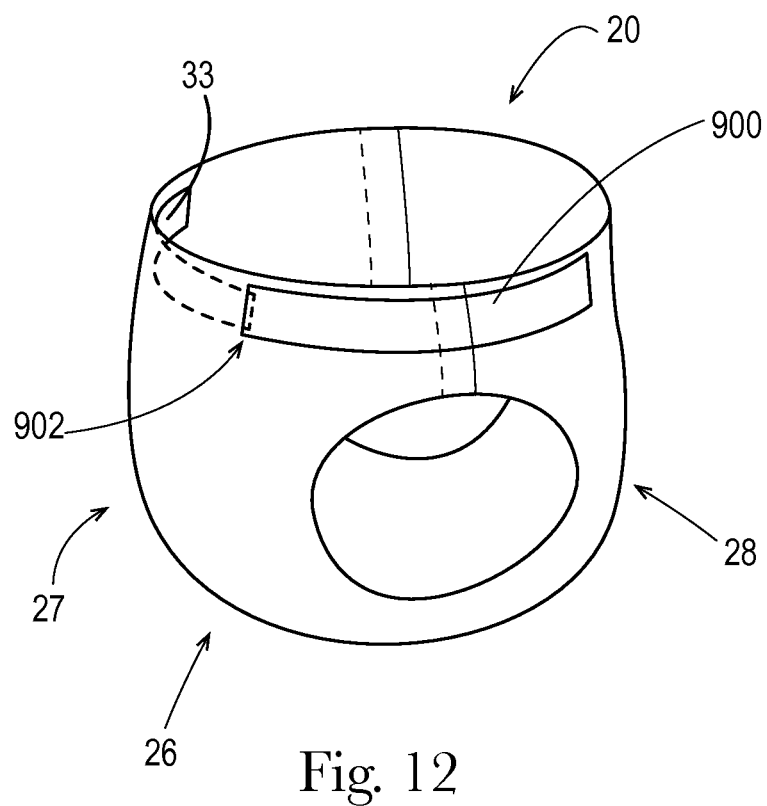
FIG. 12 is a perspective view of a reusable outer cover for a pull-on wearable pant comprising a grasping aid configured as a tab or a handle that overlaps a portion of an insert fastener component in accordance with a non-limiting embodiment of the present disclosure.

In an embodiment, referring to FIG. 12, a grasping aid 900 is shown overlapping a portion of an insert fastener component 33 indicated by arrow 902, but can overlap the full area of the insert fastener component 33. The grasping aid 900 may also overlap any number of insert fastener components, or portions thereof, in the front waist region 27, the rear waist region 28, and/or the crotch region 26 depending on the configuration of the grasping aid and the configuration of the insert fastener components. Any of the grasping aids of the present disclosure, or other grasping aids, may overlap any suitable insert fastener components on the reusable outer cover. Two grasping aids may, of course, be present and at least one or both of them may overlap at least a portion of an insert fastener component on the reusable outer cover 20. In an embodiment, the grasping aid 900 may be attached to the garment-facing surface of the reusable outer cover 20 at its end portions and may be free from attachment to the garment-facing surface of the reusable outer cover 20 in its central portion such that a finger or a portion of a hand of a wearer or caregiver can grasp the grasping aid 900 and pull up the reusable outer cover 20 (when an insert 50 is positioned within the reusable outer cover 20). Overlapping, in this context, means that either the grasping aid actually contacts a portion of the insert fastener component or is positioned on top of or below of, directly or indirectly, the insert fastener component (e.g., the insert fastener component and the grasping aid are on different layers of the reusable outer cover, but overlap each other in a direction through the reusable outer cover or the insert fastener component and the grasping aid are on opposite surfaces of the same layer of the reusable outer cover). In this context, the one or more grasping aids may be force-coupled to one or more insert fastener components so as to aid in distributing the force being applied to the grasping aid during donning and/or removal of the reusable outer cover (with an insert 50 positioned therein) from a wearer. This overlap may allow the grasping aid 200 to transfer forces received by it to the insert fastener component(s) and at least inhibit the reusable outer cover 20 from being overly stretched during donning and/or removal of the reusable outer cover 20 (i.e., when forces are applied by a wearer or a caregiver to the grasping aid).

Figure 13:
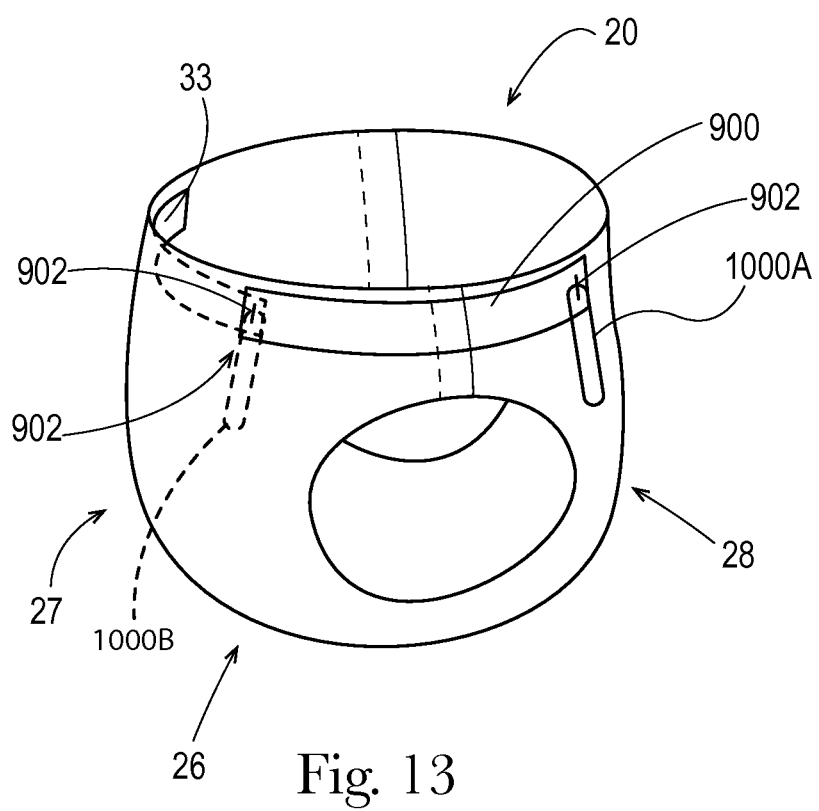
FIG. 13 is a perspective view of a reusable outer cover for a pull-on wearable pant comprising a grasping aid configured as a tab or a handle that overlaps a portion of an insert fastener component and that comprises reduced elongation zones that overlap a portion of the grasping aid in accordance with a non-limiting embodiment of the present disclosure.
Figure 14:
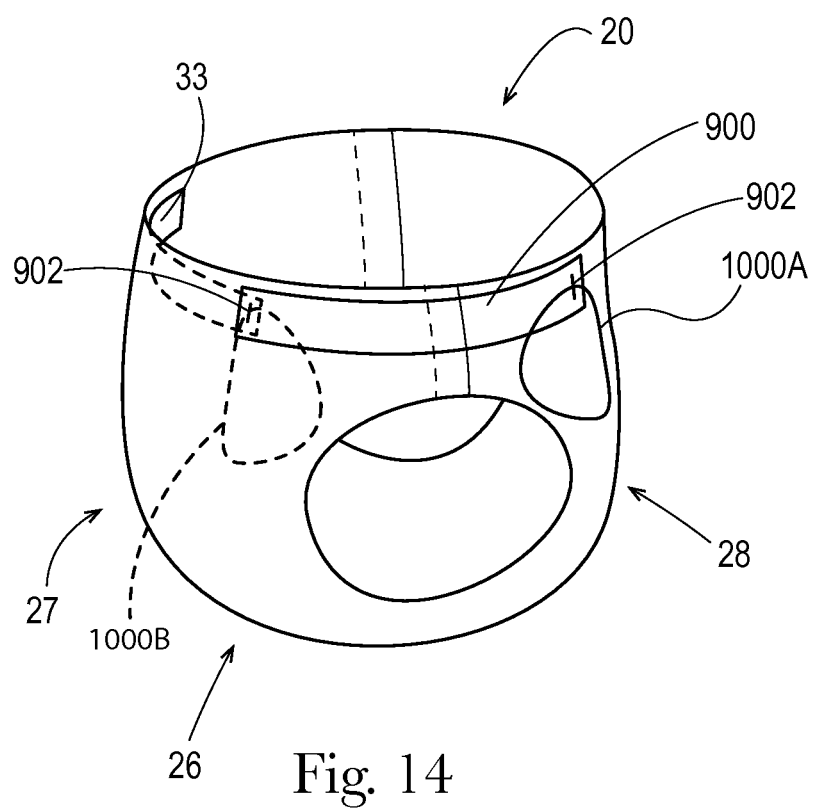
FIG. 14 is a perspective view of a reusable outer cover for a pull-on wearable pant comprising a grasping aid configured as a tab or a handle that overlaps a portion of an insert fastener component and that comprises reduced elongation zones that contact a portion of the grasping aid in accordance with a non-limiting embodiment of the present disclosure.

In an embodiment, referring to FIGS. 13 and 14, the reusable outer covers of the present disclosure may comprise one or more reduced elongation zones 1000A and 1000B. In such embodiments, a grasping aid 900 may or may not overlap or contact one or more insert fastener components 33 on the reusable outer cover 20. The reduced elongation zones may be positioned in the front waist region 27, the rear waist region 28, and/or the crotch region 26 in any suitable locations and configurations. In various embodiments, multiple reduced elongation zones may be positioned in the front and/or the rear waist regions 27 and 28 and/or in the crotch region 26. The reduced elongation zones are areas within the reusable outer cover 20 that stretch less (or exhibit less stretchability) than other portions of the reusable outer cover 20 outside of the reduced elongation zones. The reduced elongation zones can be any suitable shape or size for a particular reusable outer cover embodiment. The reduced elongation zones may comprise any non or low stretch materials, such as woven materials made out of natural or synthetic fibers, plastics, nonwovens, scrims, elastics, elastic films or laminates. The reduced elongation zones may comprise separate elements attached to one or more layers of the reusable outer cover or may comprise portions formed with or into the reusable outer cover. One or more reduced elongation zones may be positioned on each layer or only some layers of the reusable outer covers. The reduced elongation zones 1000A may be attached to the garment-facing surface of the reusable outer cover 20. The reduced elongation zones 1000B may be positioned intermediate two layers of a reusable outer cover 20 or may be positioned on the wearer-facing surface of the reusable outer cover 20. In some embodiments, either the reduced elongation zones 1000A or 1000B may be used, or both may be used in conjunction. The reduced elongation zones may be joined to portions of the reusable outer cover 20 using adhesives, stitches, bonds, hook and loop fasteners, and/or other attachments mechanism known to those of skill in the art, such as by placing materials for the reduced elongation zones into pockets formed in the reusable outer cover 20. In an embodiment, one or more portions of the reduced elongation zones 1000A and 1000B may overlap or contact points of joining 902 of the grasping aid 900 to the reusable outer cover 20. This may provide for direct force-coupling or force transfer of portions of the grasping aid 900 to portions of the reduced elongation zones 1000A and 1000B. In other instances, the reduced elongation zones 1000A and 1000B may not overlap or contact the points of joining 902, but instead may be positioned proximate to the points of joining 902 without actually overlapping or contacting them.

As stated above, the one or more grasping aids may be force-coupled to portions of, or all of, the one or more reduced elongation zones. The reduced elongation zones may reduce the amount of stress or force applied to the remainder of the reusable outer cover during donning and/or removal of the reusable outer cover (i.e., at least some of the force of donning and/or removal applied to the one or more grasping aids is transferred to the one or more reduced elongation zones). This may lead to a focusing of the applied forces (i.e., during donning) to the crotch regions and/or the disposable absorbent insert to facilitate application (i.e., facilitating the pulling of the crotch/disposable absorbent insert up between the wearer's legs). In such an embodiment, the reusable outer cover may not be overly stretched during donning and/or removal thereof when the grasping aids are used. In an embodiment, the reduced elongation zones may partially or fully overlap with and/or contact the grasping aids or portions thereof. In FIG. 9A, for example, a reduced elongation zone may partially or fully overlap the texture zone 500. The term overlap or overlapping is used here as described above. The term "contact" as used herein means to be positioned adjacent a portion of such as to touch, if on the same layer of the reusable outer cover and, if on a different layer of the reusable outer cover, to be positioned over in a direction through the reusable outer cover.

In an embodiment where the grasping aids span one or more of the seams or side seams between the front and rear waist regions 27 and 28, the reduced elongation zones may be used to transfer the forces applied to the grasping aid to the front waist region 27 and/or the rear waist region 28 and/or the crotch region 26. This feature may allow substantially even forces to be applied to the reusable outer cover when the reusable outer cover is being donned and/or removed using the one or more grasping aids. Alternatively, this feature may also be used to concentrate the transferred forces to particular zones or regions of the reusable outer cover.

In an embodiment where a grasping aid is located in the front waist region 27 and another grasping aid is located in the rear waist region 28, the reduced elongation zones may be used to transfer the forces applied to the grasping aid to the side seams or side areas of the reusable outer cover. This feature may allow substantially even forces to be applied to the reusable outer cover when the reusable outer cover is being donned and/or removed using the one or more grasping aids.

In an embodiment, the various grasping aids of the present disclosure may be attached to portions of the reusable outer cover at various locations. FIG. 15A illustrates a grasping aid 1200 (e.g., a loop, tabs, handles etc.) attached to the inner, wearer-facing surface 25 of the reusable outer cover proximate to the waist edge 21. FIG. 15B illustrates a grasping aid 1200 (e.g., a loop, tabs, handles etc.) attached to the outer, garment-facing surface 24 of the reusable outer cover proximate to the waist edge 21. FIG. 15C illustrates a grasping aid 1200 (e.g., a loop, tabs, handles etc.) attached to the reusable outer cover proximate to the waist edge 21 intermediate the inner, wearer-facing surface 25 and the outer, garment-facing surface 24. The grasping aids may be joined to the various surfaces using stitches, bonds, adhesives or other suitable attachment mechanisms 1202. It will be understood that the reusable outer covers may also comprise more than two layers or a single layer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended that the appended claims cover all such changes and modifications, and that nothing in the foregoing description or the figures, but rather, only the appended claims, limit the scope of the invention.

What is claimed is:

1. A pull-on wearable absorbent article comprising:
   a reusable outer cover comprising:
     a front waist region;
     a rear waist region;
     a crotch region disposed intermediate the front waist region and the rear waist region;
     a wearer-facing surface;
     wherein the wearer-facing surface of the front waist region or the rear waist region comprises an insert fastener component; and
     a grasping aid configured to assist in the application of the article onto a wearer, wherein the grasping aid extends from a portion of the front waist region to a portion of the rear waist region; and
   a disposable absorbent insert comprising:
     a forward region;
     a rearward region; and
     a crotch region disposed intermediate the forward region and the rearward region;
     wherein the forward region or the rearward region comprises a fastener component configured to engage the insert fastener component to attach the insert to the reusable outer cover.

2. The wearable absorbent article of claim 1, wherein the wearable absorbent article is a pant comprising permanent or releasable side seams.

3. The wearable absorbent article of claim 2, wherein the grasping aid spans one of the side seams.

4. The wearable absorbent article of claim 1, wherein the grasping aid extends from the reusable outer cover.

5. The wearable absorbent article of claim 1, wherein the grasping aid is formed in or on the reusable outer cover.

6. The wearable absorbent article of claim 1, wherein the grasping aid comprises an aperture formed in the reusable outer cover.

7. The wearable absorbent article of claim 1, wherein the grasping aid forms a loop or a pocket and is configured to receive one or more fingers.

8. The wearable absorbent article of claim 1, comprising a second grasping aid, wherein the grasping aid is positioned on a first side of a longitudinal axis of the reusable outer cover, and wherein the second grasping aid is positioned on a second side of the longitudinal axis of the reusable outer cover.

9. The wearable absorbent article of claim 1, wherein a portion of the grasping aid overlaps the insert fastener component and is force-coupled to the insert fastener component.

10. The wearable absorbent article of claim 1, wherein the grasping aid comprises a first end and a second end, wherein the reusable outer cover comprises a portion, wherein the grasping aid is joined to the portion at the first end and at the second end, and wherein a central portion of the grasping aid is free from attachment to the portion of the reusable outer cover and forms a loop between the first end and the second end.

11. The wearable absorbent article of claim 1, wherein the grasping aid comprises a first end and a second end, wherein the reusable outer cover comprises a portion, wherein the grasping aid is attached to the portion at the first end and at the second end, and wherein a central portion of the grasping aid forms a pocket configured to receive one or more fingers.

12. The wearable absorbent article of claim 1, wherein a portion of the grasping aid is formed from a portion of the reusable outer cover.

13. The wearable absorbent article of claim 1, wherein the grasping aid has a first elastic modulus, wherein the reusable outer cover has a second elastic modulus, and wherein the first elastic modulus and the second elastic modulus are different.

14. The wearable absorbent article of claim 1, wherein the grasping aid comprises a zone positioned on a surface of the reusable outer cover, and wherein the zone comprises areas having a higher coefficient of friction than other portions of the surface outside of the zone.

15. The wearable absorbent article of claim 1, wherein the grasping aid comprises a textured zone positioned on a surface of the reusable outer cover.

16. The wearable absorbent article of claim 15, wherein the textured zone comprises one or more ridges, bumps, or raised portions.

17. A pull-on wearable absorbent article, comprising:
    a reusable outer cover comprising:
      a front waist region;
      a rear waist region;
      a crotch region disposed intermediate the front waist region and the rear waist region;
      a wearer-facing surface;
      wherein the wearer-facing surface of the front waist region or the rear waist region comprises an insert fastener component;
      a reduced elongation zone; and
      a first grasping aid configured to assist in the application of the article onto a wearer;
      a second grasping aid configured to assist in the application of the article onto the wearer, wherein the first grasping aid is positioned on a first side of a lateral axis of the reusable outer cover, and wherein the second grasping aid is positioned on a second side of the lateral axis of the reusable outer cover; and
    a disposable absorbent insert comprising:
      a forward region;
      a rearward region; and
      a crotch region disposed intermediate the forward region and the rearward region;
      wherein the forward region or the rearward region comprises a fastener component configured to engage the insert fastener component to attach the insert to the reusable outer cover.

18. The wearable absorbent article of claim 17, comprising a second reduced elongation zone.

19. The wearable absorbent article of claim 18, wherein the first or second grasping aid is force-coupled to the insert fastener component.

20. A reusable outer cover configured for use with a disposable absorbent insert, the outer cover configured as a pull-on pant and comprising:
    a front waist region;
    a rear waist region;
    a crotch region disposed intermediate the front waist region and the rear waist region;
    a wearer-facing surface;

wherein the wearer-facing surface of the front waist region or the rear waist region comprises an insert fastener component; and a grasping aid configured to assist in the application of the article onto a wearer, wherein the grasping aid is force-coupled to the insert fastener component.

21. A pull-on wearable absorbent article comprising:
the reusable outer cover of claim 20; and
a disposable absorbent insert comprising:
   a forward region;
   a rearward region; and
   a crotch region disposed intermediate the forward region and the rearward region;
   wherein the forward region or the rearward region comprises a fastener component configured to engage the insert fastener component to attach the insert to the reusable outer cover.

* * * * *